(12) United States Patent
Schlegel et al.

(10) Patent No.: US 9,279,106 B2
(45) Date of Patent: Mar. 8, 2016

(54) IMMORTALIZATION OF EPITHELIAL CELLS AND METHODS OF USE

(75) Inventors: Richard Schlegel, Rockville, MD (US); Xuefeng Liu, Gaithersburg, MD (US)

(73) Assignee: Georgetown University, Washington, DC (US)

(*) Notice: Subject to any disclaimer, the term of this patent is extended or adjusted under 35 U.S.C. 154(b) by 140 days.

(21) Appl. No.: 13/885,078

(22) PCT Filed: Nov. 11, 2011

(86) PCT No.: PCT/US2011/060378
§ 371 (c)(1),
(2), (4) Date: Jul. 24, 2013

(87) PCT Pub. No.: WO2012/065067
PCT Pub. Date: May 18, 2012

(65) Prior Publication Data
US 2013/0309681 A1 Nov. 21, 2013

Related U.S. Application Data

(60) Provisional application No. 61/413,291, filed on Nov. 12, 2010, provisional application No. 61/474,901, filed on Apr. 13, 2011.

(51) Int. Cl.
| | | |
|---|---|---|
| *A61K 35/36* | (2015.01) | |
| *A61P 17/00* | (2006.01) | |
| *A61P 17/02* | (2006.01) | |
| *C12N 5/071* | (2010.01) | |
| *C12Q 1/68* | (2006.01) | |
| *G01N 33/50* | (2006.01) | |

(52) U.S. Cl.
CPC .............. *C12N 5/0683* (2013.01); *C12N 5/067* (2013.01); *C12N 5/0625* (2013.01); *C12N 5/0631* (2013.01); *C12N 5/0688* (2013.01); *C12Q 1/6883* (2013.01); *G01N 33/5091* (2013.01); *C12N 2500/05* (2013.01); *C12N 2500/40* (2013.01); *C12N 2501/01* (2013.01); *C12N 2501/11* (2013.01); *C12N 2501/33* (2013.01); *C12N 2501/39* (2013.01); *C12N 2501/727* (2013.01); *C12N 2502/1323* (2013.01); *C12N 2502/16* (2013.01); *C12N 2503/02* (2013.01); *C12N 2510/04* (2013.01); *C12Q 2600/106* (2013.01); *C12Q 2600/158* (2013.01)

(58) Field of Classification Search
CPC ........... C12N 2500/40; C12N 2501/01; C12N 2501/11; C12N 2501/33; C12N 2501/39; C12N 2501/727; C12N 2502/1323; C12N 2510/04; C12N 5/0625; C12N 5/0631; C12N 5/067; C12N 5/0683; C12N 5/0688
USPC .................................................. 435/375, 377
See application file for complete search history.

(56) References Cited

U.S. PATENT DOCUMENTS

| | | | | |
|---|---|---|---|---|
| 2010/0112691 | A1* | 5/2010 | Green et al. ............ | 435/377 |
| 2010/0124781 | A1 | 5/2010 | Nelson | |
| 2010/0272695 | A1* | 10/2010 | Agulnick et al. ............ | 424/93.7 |

FOREIGN PATENT DOCUMENTS

| | | | |
|---|---|---|---|
| WO | 2010/053472 A1 † | 5/2010 | |
| WO | 2010/065907 A2 † | 6/2010 | |

OTHER PUBLICATIONS

Chapman et al. (2010) Human Keratinocytes are Efficiently Imortalized by a Rho Kinase Inhibitor, J. Clin. Invest., 120 (7):2619-2626.
International Application No. PCT/US11/60378, International Search Report and Written Opinion dated Jun. 6, 2012.
Shi, J., Wei, L., Rho kinase in the regulation of cell death and survival, 24 pages (pp. 61-75), Mar. 9, 2007, Arch. Immunol. Ther. Exp. (Warsz). 55(2).†
Terunuma, A., et al, Efficient procurement of epithelial stem cells from human tissue specimens using a Rho-associated protein kinase inhibitor Y-27632, 6 pages (pp. 1363-1368), Jan. 1, 2010, Tissue Eng. 16.†
Watanabe, K., et al, A ROCK inhibitor permits survival of dissociated human embryonic stem cells, 6 pages (pp. 681-686), May 27, 2007, Nature Publishing Group, Nature Biotech. 25.†
Xia, L., et al, Isolation of human sebaceous glands and cultivation of sebaceous gland-derived cells as an in vitro model, 8 pages (pp. 315-321), Sep. 1, 1989, The Society for Investigative Dermatology, Inc., J. Invest. Dermatol. 93.†
Chapman, S., Liu, X., Meyers, C., Schlegel, R., McBride, A.A., Human keratinocytes are efficiently immortalized by a Rho kinase inhibitor, 8 pages (pp. 2619-2626), Jul. 1, 2010, American Society for Clinical Investigation, J.Clin. Investig. 120(7).†
Fu, B., et al, Keratinocyte growth conditions modulate telomerase expression, senescence, and immortalization by human papillomavirus type 16 E6 and E7 oncogenes, 10 pages (pp. 7815-7824), Nov. 15, 2003, American Association for Cancer Research.†
Herbert, B-S., Wright, W.E., Shay, J.W., p16INK4a inactivation is not required to immortalize human mammary epithelial cells, 4 pages (pp. 7897-7900), Nov. 7, 2002, Nature Publishing Group, Oncogene 21.† Luengo Gemino, F., et al, One-year follow-up of epithelial corneal cell sheet allografts mounted on platelet poor plasma in rabbits, 9 pages (pp. 2771-2779), Dec. 15, 2009, Molecular Vision, Molecular Vision 15.†
McMullan, R., et al, Keratinocyte differentiation is regulated by the Rho and ROCK signaling pathway, 5 pages (pp. 2185-2189), Dec. 16, 2003, Elsevier Science Ltd., Current Biology 13.†
Narumiya, S., Ishizaki, T., Uehata, M., Use and properties of ROCK-specific inhibitor Y-27632, 12 pages (pp. 273-284), Feb. 1, 2000, Academic Press, Methods Enzymol. 325.†
Olson, M.F., Applications for ROCK kinase inhibition, 7 pages (pp. 242-248), Feb. 20, 2008, Elsevier Ltd., Curr. Opin. Cell Biol. 20.†
Ramirez, R.D., et al, Putative telomere-independent mechanisms of replicative aging reflect inadequate growth conditions, 6 pages (pp. 398-403), Feb. 15, 2001, Cold Spring Harbor Laboratory Press, Genes & Development 15.†

\* cited by examiner
† cited by third party

*Primary Examiner* — Janet Epps-Smith
(74) *Attorney, Agent, or Firm* — Morgan, Lewis & Bockius LLP

(57) ABSTRACT

The present invention is directed towards methods of culturing non-keratinocyte epithelial cells, with the methods comprising culturing non-keratinocyte epithelial cells in the presence of feeder cells and a calcium-containing medium while inhibiting the activity of Rho kinase (ROCK) in the feeder cell, the non-keratinocyte epithelial cells or both during culturing.

10 Claims, 31 Drawing Sheets

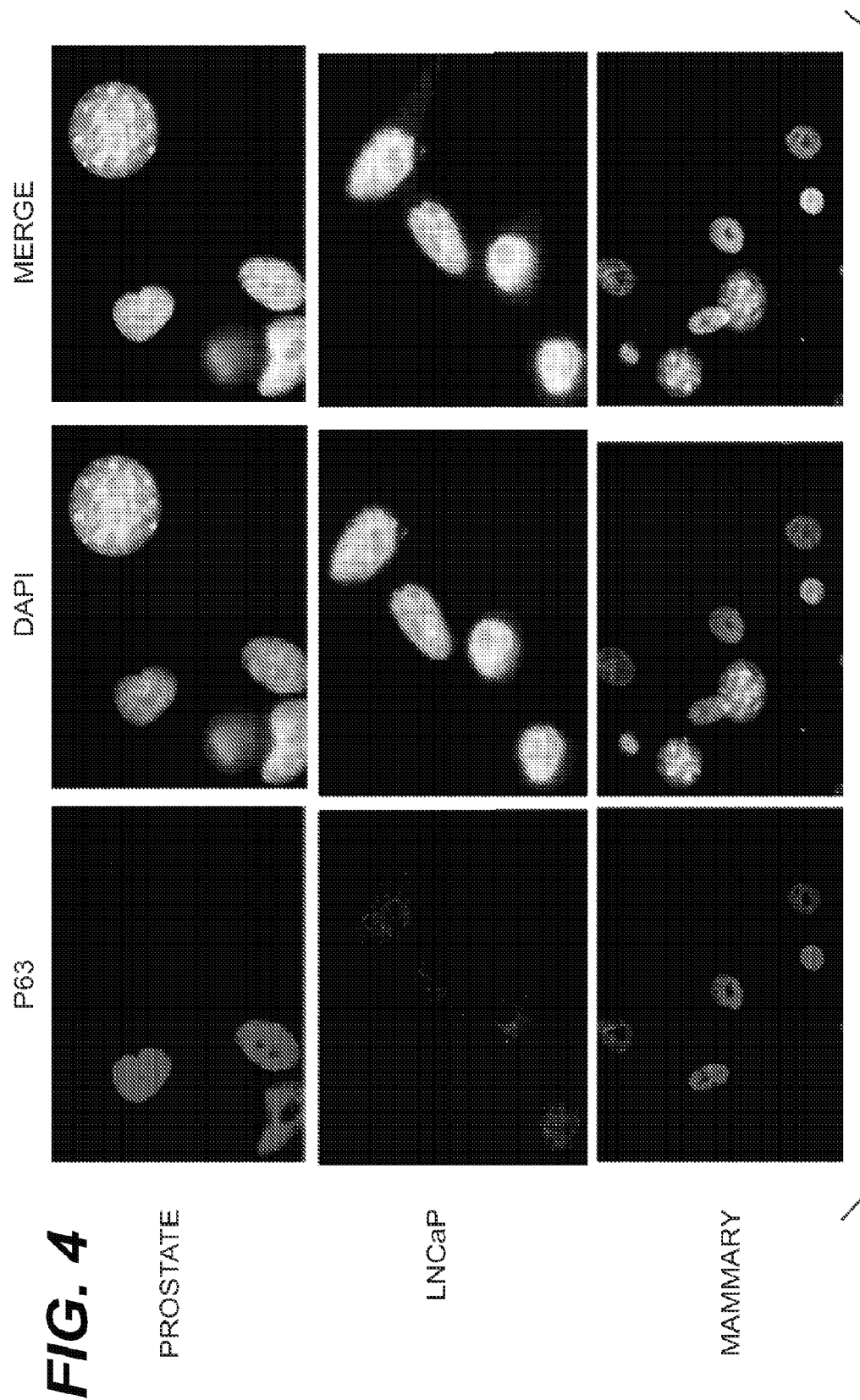

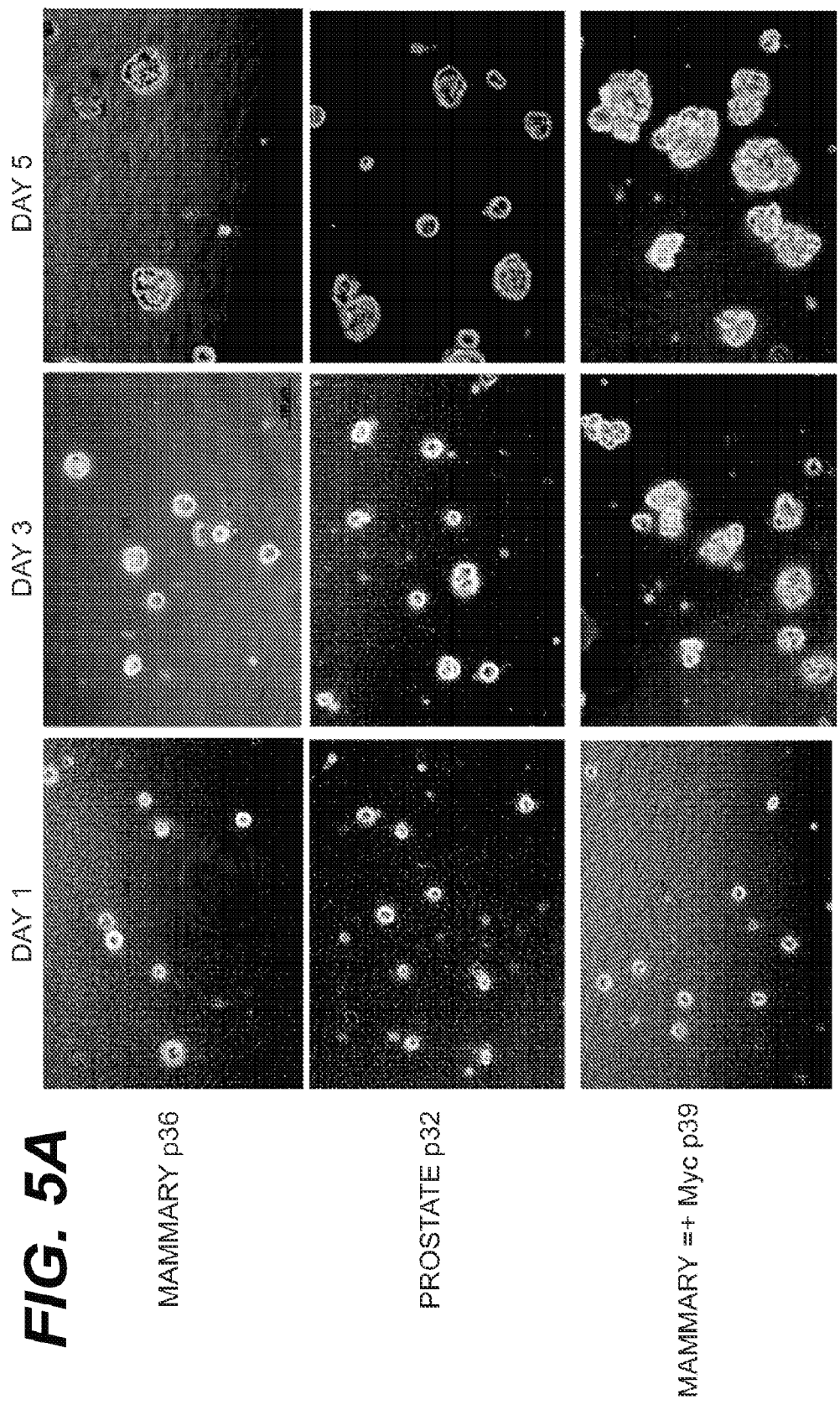

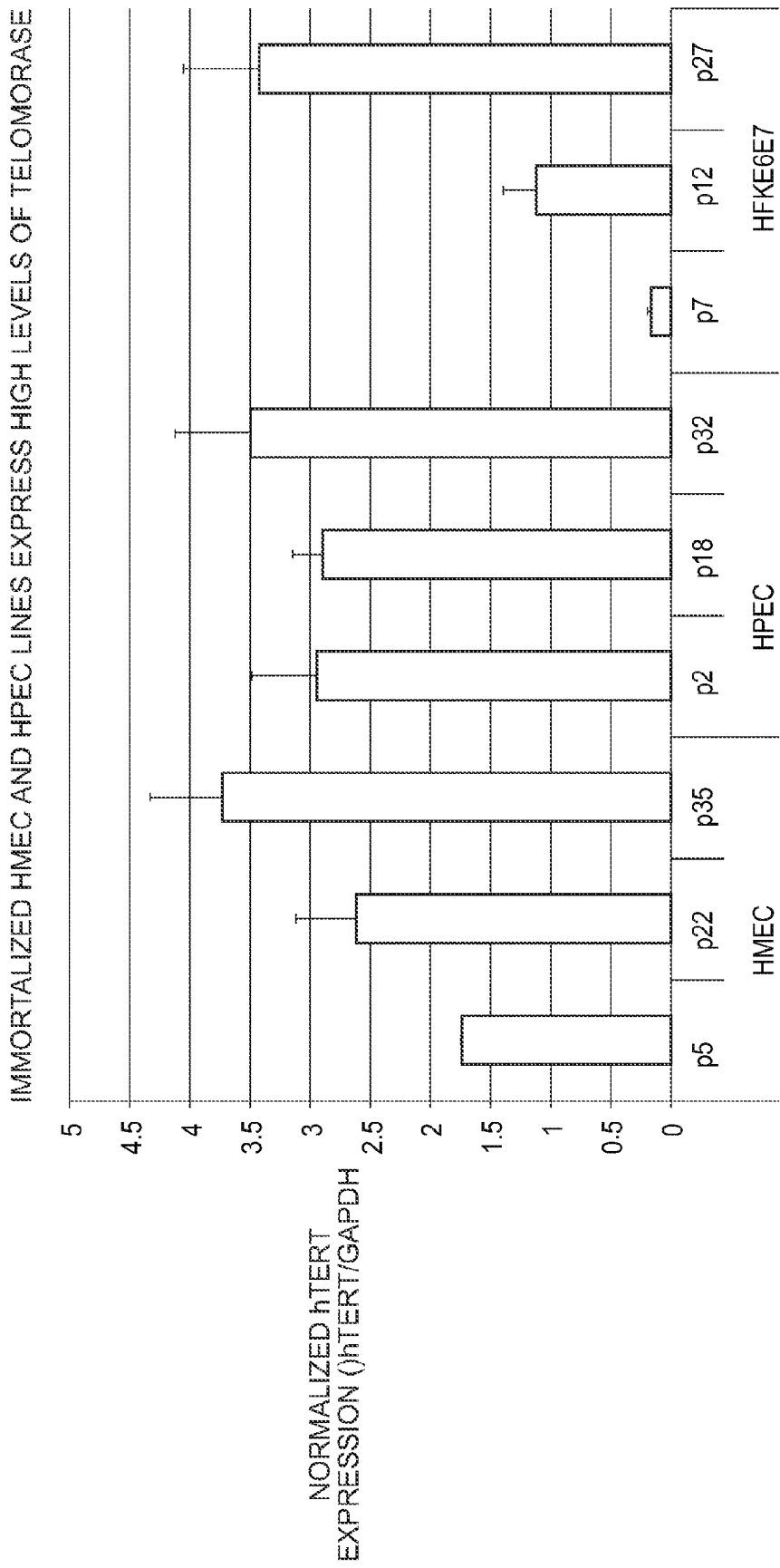

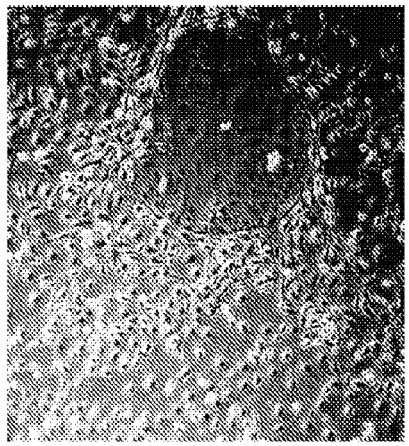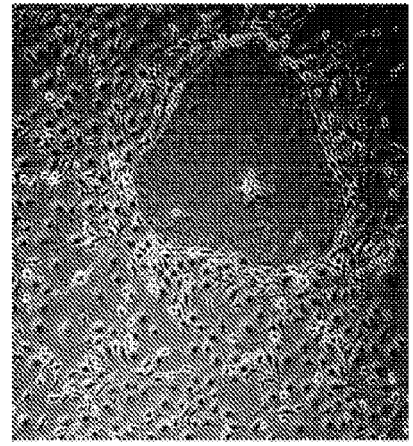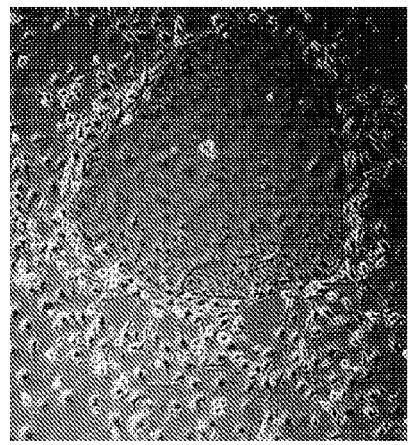
FIG. 8

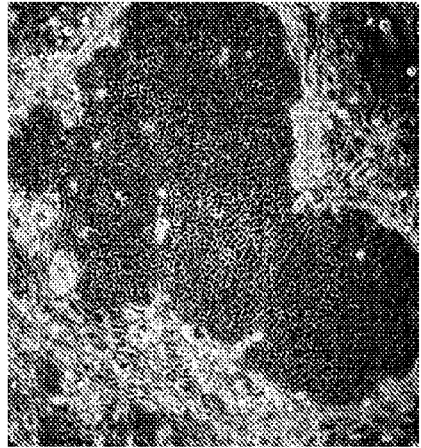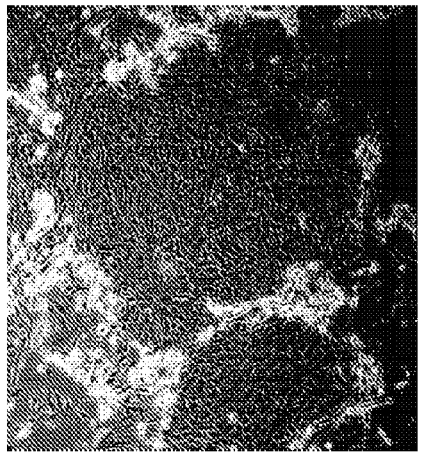
FIG. 9

IMMORTALIZATION OF EPITHELIAL CELLS AND METHODS OF USE

CROSS-REFERENCE TO RELATED APPLICATIONS

This applications claims priority to U.S. Provisional Application Ser. Nos. 61/413,291, filed 12 Nov. 2010 and 61/474,901, filed 13 Apr. 2011, both of which are incorporated by reference.

STATEMENT REGARDING FEDERALLY SPONSORED RESEARCH OR DEVELOPMENT

Part of the work performed during development of this invention utilized U.S. Government funds under National Institutes of Health Grant Nos. R01CA106400 and R01-CA053371. The U.S. Government has certain rights in this invention.

BACKGROUND OF THE INVENTION

1. Field of the Invention

The present invention is directed towards methods of culturing non-keratinocyte epithelial cells, with the methods comprising culturing non-keratinocyte epithelial cells in the presence of feeder cells and a calcium-containing medium while inhibiting the activity of Rho kinase (ROCK) in the feeder cell, the non-keratinocyte epithelial cells or both during culturing. The present invention is also directed towards methods of using these immortalized non-keratinocyte epithelial cells.

2. Background of the Invention

Vital organs like the lung, the kidney, liver, pancreas and the skin are characterized by, among other things, the presence of organ-specific differentiated epithelial cells. The differentiated epithelial cells are of course related to the specific function of each such organ. The specific functions may be as varied as, for example, gas exchange in the lung, filtration in the kidney, detoxification and conjugation in the liver, insulin production in the pancreatic islet cells or protection against a hazardous environment by the skin. Disease or degeneration of such an organ is often life threatening because degenerated or lost organ structure is often poorly replaced and because the specialized cells of one organ cannot take over the function of another organ.

Differentiated cells such as kidney epithelial cells, insulin-producing cells in the Islets of Langerhans of the pancreas, and glandular and/or hair follicle cells of the dermis are difficult to recover, if possible at all, and even more difficult to maintain once taken out of their context in the body. Indeed, differentiated epithelial cells have a very limited lifespan in culture. Generally speaking, epithelial cells, other than keratinocytes, harvested from animals can be grown in culture perhaps through only one or two passages.

To study non-keratinocyte epithelial (NKE) cells in vitro, some type of genetic manipulation such as inserting viral or cellular oncogenes, is required to allow the cells to survive more than a few passages. These genetic manipulations, however, change the cells' genetic background as well as physiology such that cells may not resemble or function like normal epithelial cells. Moreover, these genetically-modified cells would not be candidates for implantation into an intact animal.

What is needed in the art are methods of culturing NKE cells harvested from organs for extended periods of time, without having the genetically alter the cells. The present invention solves the problems associated with culturing NKE cells for extended periods of time without the need for genetic manipulation.

SUMMARY OF THE INVENTION

The present invention is directed towards methods of culturing non-keratinocyte epithelial cells, with the methods comprising culturing non-keratinocyte epithelial cells in the presence of feeder cells and a calcium-containing medium while inhibiting the activity of Rho kinase (ROCK) in the feeder cell, the non-keratinocyte epithelial cells or both during culturing.

The present invention is also directed towards methods of producing conditionally immortalized non-keratinocyte epithelial cells, with the methods comprising culturing non-keratinocyte epithelial cells in the presence of feeder cells and a calcium-containing medium while inhibiting the activity of ROCK in the feeder cells, the non-keratinocyte epithelial cells or both. Culturing the non-keratinocyte epithelial cells in such conditions will produce conditionally immortalized non-keratinocyte epithelial cells.

The present invention is also directed towards methods of producing at least partially differentiated non-keratinocyte epithelial cells comprising culturing for a set time non-keratinocyte epithelial cells in the presence of feeder cells and a calcium-containing medium while inhibiting the activity of ROCK in the feeder cells, the non-keratinocyte epithelial cells or both to produce conditionally immortalizing non-keratinocyte epithelial cells. After culturing the conditionally immortalized non-keratinocyte epithelial cells in these conditions, the conditionally immortalized non-keratinocyte epithelial cells are placed in conditions that promote differentiation of the conditionally immortalized non-keratinocyte epithelial cells.

The present invention is also directed towards methods of stimulating growth of non-keratinocyte epithelial cells, with the methods comprising culturing non-keratinocyte epithelial cells in the presence of feeder cells and a calcium-containing medium while inhibiting the activity of ROCK in the feeder cells, the non-keratinocyte epithelial cells or both. Culturing the non-keratinocyte epithelial cells in such conditions will stimulate non-keratinocyte epithelial cells to grow, whereas otherwise the cells may not grow.

BRIEF DESCRIPTION OF THE DRAWINGS

FIG. 4 depicts cell surface marker expression of late passage normal human prostate epithelial cells (HPEC) (passage 29) and normal human mammary epithelial cells (HMEC) (passage 32) using the methods and culture conditions disclosed herein. An established human prostate cancer cell line (LNCaP) was used as a control. Cells were stained for the basal epithelial cell marker P63 (P63 column) and for DNA (DAPI column). The column on the right is a merge of the two images. Both the HPECs and HMECs were late passage cells. These late passage HPEC and HMEC cells still exhibit the P63 marker even after over 80 passages, indicating that the cells still resemble normal basal, stem-like epithelial cells. The large round cell in the top right portion of the middle panel of the top row is a feeder cell. The splotchy DAPI staining of the non-proliferating feeder cell shows that the DNA has been fragmented.

FIG. 8 depicts the growth and maintenance of mouse hepatic epithelial cells using the methods and culture conditions disclosed herein. Each panel represents hepatocytes harvested from C57BL/6 mice with distinct genetic backgrounds. wt: wild-type cells at passage 2, D: hepatocytes from liver-specific knockout mouse of STAT3 (signal transducer and activator of transcription 3) at passage 2, Elf+/−: hepatocytes from heterozygous knockout mouse of ELF (which is a beta-spectrin) at passage 2, L−/−: hepatocytes from progeny of cross between the "ELF+/−" and "D" mice at passage 2. All cells were grown in F medium supplemented with 5% fetal bovine serum and in the presence of the ROCK inhibitor Y27632 at a concentration of 10 μM. At the center of each panel, epithelial cells are growing in clusters that are surrounded by mouse fibroblast feeder cells.

FIG. 9 depicts the growth and maintenance of mouse mammary epithelial cells using the methods and culture conditions disclosed herein. Each panel represents mammary epithelial harvested from mice with distinct genetic backgrounds. mMEC FVB: mammary cells from wild-type FVB strain at passage 2, mMEC 43: mammary cells from transgenic mice overexpressing an active isoform of AIB1 ("amplified in breast cancer factor 1") where exon three was deleted at passage 2, mMEC AIB up: mammary cells from transgenic mice containing a construct with a tet-inducible AIB1 transgene at passage 2, her2/neu: mammary cells from transgenic mice overexpressing her2/neu at passage 2. All cells were grown in F medium supplemented with 5% fetal bovine serum and in the presence of the ROCK inhibitor Y27632 at a concentration of 10 μM. At the center of each panel, epithelial cells are growing in clusters that are surrounded by mouse fibroblast feeder cells.

FIG. 16 shows that the early E6 and E7 transforming genes were being transcribed but that the L1 gene was not.

DETAILED DESCRIPTION OF THE INVENTION

Figure 1:
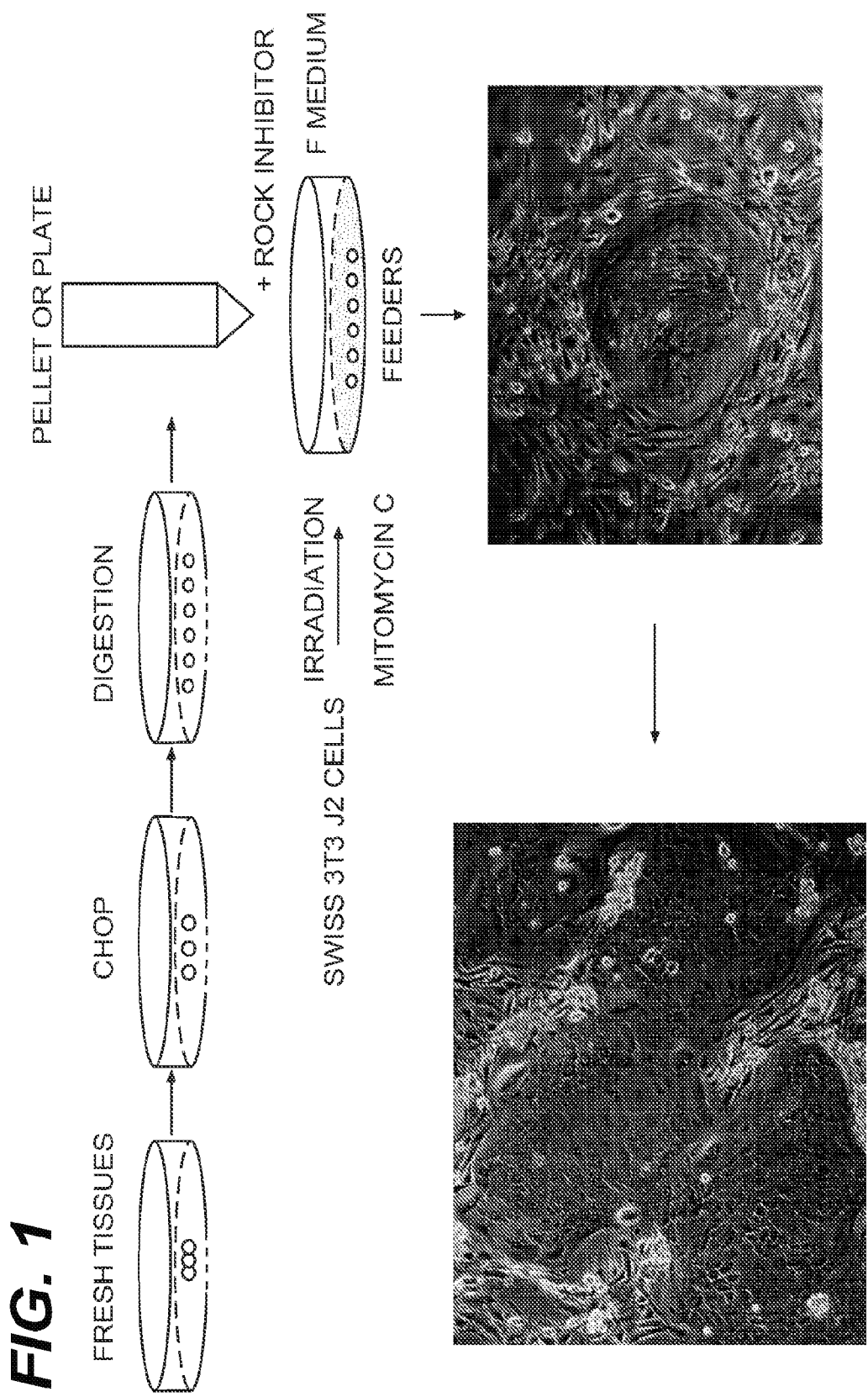
FIG. 1 depicts a flow diagram of one embodiment of the methods of the present invention.

The present invention is directed towards methods of culturing non-keratinocyte epithelial cells, with the methods comprising culturing non-keratinocyte epithelial cells in the presence of feeder cells and a calcium-containing medium while inhibiting the activity of Rho kinase (ROCK) in the feeder cell, the non-keratinocyte epithelial cells or both during culturing.

As used herein, the term "epithelium" or "epithelial cell" refers to a cell or cells that line hollow organs, as well as those that make up glands and the outer surface of the body. In general, there can be considered four types of epithelial cells: squamous epithelial cells, columnar epithelial cells, adenomatous epithelial cells and transitional epithelial cells. Epithelial cells can be arranged in single or multiple layers, depending on the organ and location. Keratinocytes are the cells that compose the squamous epithelium that is found at anatomic sites such as the skin, esophagus and cervix. Keratinocytes terminally differentiate into flat, highly keratinized, non-viable cells that help protect against the environment and infection by forming a protective barrier. The present invention is directed to any type of non-keratinocyte epithelial cells ("NKE cell"). NKE cells form the glandular epithelium of the body such as found in the breast, prostate, liver, and gastrointestinal tract. NKE cells differentiate into functional, viable cells that can either function in absorption and/or secretion and these cells do not form highly keratinized structures characteristic of squamous epithelial cells. The phrase "non-keratinocyte epithelial cell" is well-understood in the art and one of ordinary skill in the art would readily understand the common, ordinary meaning of the term. The NKE cells used in the methods of the present invention can be of any type or tissue of origin.

Examples of NKE cells that are encompassed by the term as used herein include but are not limited to prostate cells, mammary cells, hepatocytes, pancreatic islet cells including beta cells, pulmonary epithelial cells, kidney cells, bladder cells, stomach epithelial cells, large and small intestinal epithelial cells, urethral epithelial cells, testicular epithelial cells, ovarian epithelial cells, cervical epithelial cells, thyroid cells, parathyroid cells, adrenal cells, thymus cells, gall bladder cells, pituitary cells.

The cells can be from any animal, including but not limited to any mammal, such as mouse, rat, canine, feline, bovine, equine, porcine, non-human and human primates. Mammalian cells particularly suitable for cultivation in the present media include epithelial cells of human origin, which may be primary cells derived from a tissues such as but not limited to mammary glands, prostate glands, liver, pancreas, kidney, bronchi and trachea. In addition, transformed cells or established cell lines, e.g., HeLa cervical epithelial cell lines can also be used. The cells used in the present invention may be normal, healthy cells that are not diseased or not genetically altered, or the cells may be diseased or genetically altered. Accordingly, "diseased epithelial cells" are a subset of NKE cells herein. "Diseased cells" means that the cells are from abnormal tissue, such as from a neoplasia, a hyperplasia or malignant tumor or benign tumor including, but not limited to, diseased cells isolated from the circulation, i.e., circulating tumor cells (CTC's), of an animal. Other mammalian cells such as but not limited to CHO cells, COS cells, VERO cells, BHK cells (including BHK-21 cells) and derivatives or subclones thereof are also suitable for the methods of the present invention. In one embodiment, the cells are primary or secondary human NKE cells from a sample of normal or abnormal tissue. In another embodiment, the cells are not primary cells, such as cells from an established cell line, transformed cells, thawed cells from a previously frozen collection and the like. Animal cells for culturing by the present invention may be obtained commercially, for example from ATCC (Rockville, Md.), Cell Systems, Inc. (Kirkland, Wash.), Clonetics Corporation (San Diego, Calif.), BioWhittaker (Walkersville, Md.) or Cascade Biologicals (Portland, Oreg.).

As used herein, primary cells are cells that have been taken directly from living tissue, such as a biopsy or isolated from circulation, and have not been passaged or only passaged one time. Thus, primary cells have been freshly isolated, often through tissue digestion and plated. Provided the cells have been passaged one time or less, primary cells may or may not be frozen and then thawed at a later time. In addition, the tissue from which the primary cells are isolated may or may not have been frozen of preserved in some other manner immediately prior to processing.

The NKE cells for use the present invention are not undifferentiated, embryonic stem cells. Thus, the phrase non-keratinocyte epithelial cell as used herein automatically excludes undifferentiated embryonic stem cells. As used herein and in the art, embryonic stem cells are undifferentiated cells that have the capacity to regenerate or self-renew indefinitely. The NKE cells used in the methods herein may or may not be adult stem cells. As used herein, adult stem cells are isolated from tissues of an animal and are less differentiated than completely differentiated cells, but are more differentiated than embryonic stem cells. In one embodiment, the NKE cells cultured according to the methods of the present invention are adult stem cells. In another embodiment of the present invention the NKE cells cultured according to the methods of the present invention are not adult stem cells. The NKE cells used in the present invention would not normally have the capacity for indefinite self-renewal. Moreover, the NKE cells are not completely undifferentiated cells upon initial isolation and plating in that the cells will possess cell surface markers not typically associated with undifferentiated stem cells, or conversely the NKE cells do not possess cell surface markers typically associated with undifferentiated stem cells.

When isolating primary cells, tissue should ideally be handled using standard sterile techniques and a laminar flow safety cabinet. In one embodiment, a single needle biopsy is sufficient to isolate enough primary cells to begin the cell culture methods of the present invention. In the case of a tissue biopsy, tissue can be cut into small pieces using sterile instruments. In another embodiment, a single cell isolated from the circulation of a subject is sufficient material to begin the cell culture methods of the present invention. The small pieces can then be washed several times with sterile saline solution or other buffer, such as PBS, that may or may not be supplemented with antibiotics or other ingredients. After washing, the pieces are often, but need not be, treated with an enzymatic solution such as, but not limited to collagenase, dispase or trypsin, to promote dissociation of cells from the tissue matrix.

Dispase is often used to dissociate epithelium from the underlying tissue. This intact epithelium may then be treated with trypsin or collagenase. These digestion steps often results in a slurry containing dissociated cells and tissue matrix. The slurry can then be centrifuged with sufficient force to separate the cells from the remainder of the slurry. The cell pellet can then be removed and washed with buffer and/or saline and/or cell culture medium. The centrifuging and washing can be repeated any number of times. After the final washing, the cells can then be washed with any suitable cell culture medium. Of course, the digestion and washing steps need not be performed if the cells are sufficiently separated from the underlying tissue upon isolation, such as the case in a needle biopsy or if isolated from the circulation. For example, cells such as tumor cells may be isolated from the circulation of the organism using currently available techniques for isolating cells that express cell markers that are specific for a specific type of tumor cell. See Lu. J., et al., *Int'l. J. Cancer,* 126(3):669-683 (2010) and Yu, M., et al., *J. Cell Biol.,* 192(3): 373-382 (2011), which are incorporated by reference. Cells may or may not be counted using an electronic cell counter, such as a Coulter Counter, or they can be counted manually using a hemocytometer. Of course, the cells need not be counted at all.

For the purposes of the present invention cells are no longer considered to be primary cells after the cells have been passaged more than once. In addition, cells passaged once or more and immediately frozen after passaging are also considered not to be primary cells when thawed. In select embodiments of the present invention, the NKE cells are initially primary cells and, through the use of the methods of the present invention, become non-primary cells after passaging.

By "cell culture" or "culture" is meant the maintenance of cells in an artificial, in vitro environment. The term "cell culture" also encompasses cultivating individual cells and tissues.

The cells being cultured according to the present invention, whether primary or not, can be cultured and plated according to the experimental conditions as needed by the technician. The examples herein demonstrate at least one functional set of culture conditions that can be used in conjunction with the methods described herein. If not known, plating and culture conditions for a given animal cell type can be determined by one of ordinary skill in the art using only routine experimentation. Cells may or may not be plated onto the surface of culture vessels using attachment factors. If attachment factors are used, the culture vessels can be precoated with a natural, recombinant or synthetic attachment factor or factors or peptide fragments thereof, such as but not limited to collagen, fibronectin and natural or synthetic fragments thereof.

The cell seeding densities for each experimental condition can be manipulated for the specific culture conditions needed. For routine culture in plastic culture vessels, an initial seeding density of from about $1 \times 10^4$ to about $1-10 \times 10^5$ cells per $cm^2$ is fairly typical, e.g., $1 \times 10^6$ cells are often cultured in a 75 $cm^2$ culture flask. Using the methods of the present invention, however, even a single cell can be plated initially. Thus, the methods of the present invention can be performed using 1, 2, 3, 4, 5, 6, 7, 8, 9, 10, 20, 30, 40, 50, 60, 70, 80, 90, 100 or more cells for an initial cell seeding. Of course, higher cell seeding numbers can be used, such as but not limited to $1 \times 10^3$, $1 \times 10^4$, $1 \times 10^5$ and so on. Cell density can be altered as needed at any passage.

Mammalian cells are typically cultivated in a cell incubator at about 37° C. at normal atmospheric pressure. The incubator atmosphere is normally humidified and often contain about from about 3-10% carbon dioxide in air. Temperature, pressure and $CO_2$ concentration can be altered as necessary, provided the cells are still viable. Culture medium pH can be in the range of about 7.1 to about 7.6, in particular from about 7.1 to about 7.4, and even more particular from about 7.1 to about 7.3.

Cell culture medium is normally replaced every 1-2 days or more or less frequently as required by the specific cell type. As the NKE cells approach confluence in the culture vessel, they are normally passaged. As used herein a cell passage is used as it is in the art and means splitting or dividing the cells and transferring a portion of the cells into a new culture vessel or culture environment. Most likely, the NKE cells used in the methods of the present invention will be adherent to the cell culture surface and will need to be detached. Methods of detaching adherent cells from the surface of culture vessels are well-known and commonly employed and can include the use of enzymes such as trypsin.

A single passage refers to when a technician splits or manually divides the cells one time and transfers a smaller number of cells into a new vessel or environment. When passaging, the cells can be split into any ratio that allows the cells to attach and grow. Thus, at a single passage the cells can be split in a 1:2 ratio, 1:3, 1:4, 1:5 etc. Passaging cells, therefore, is not equivalent to population doubling. As used herein a population doubling is when the cells divide in culture one time such that the number of cells in culture is approximately doubled. Cells need to be counted to determine if a population of cells has doubled, tripled or multiplied by some other factor. In other words, passaging the cells and splitting them in a 1:3 ratio for further culturing in vitro is not to be taken as the equivalent that the cell population has tripled.

In one embodiment of the present invention, the NKE cells are continuously cultured in vitro. As used herein, "continuous culturing" is the notion that the cells continually divide and reach or approach confluence in the cell culture vessel such that the cells require passaging and fresh medium to maintain their health. Thus, the concept of "continuously culturing" is similar to the concept that the NKE cells would be immortalized. In one embodiment, when cultured using the present methods and conditions of the present invention, normal NKE cells can continue to grow and divide for at least 5, 10, 15, 20, 25, 30, 35, 40, 45, 50, 55, 60, 65, 70, 75, 80, 85, 90, 95, 100, 125, 150, 175, 200, 250 or 300 passages or more.

The present invention is also directed towards methods of stimulating growth of NKE cells, in particular normal NKE cells, in vitro with the methods comprising culturing the NKE cells in the presence of feeder cells and a calcium-containing medium while inhibiting the activity of ROCK in the feeder cells, the NKE cells or both. Culturing the NKE cells in such conditions will stimulate the NKE cells to grow or proliferate, whereas otherwise the cells may not grow. In one specific embodiment, the cells grow in tight clusters, i.e., the cells become tightly adherent. In one embodiment, the cultured NKE cells form junctions involving e-cadherin, non muscle myosin, and p120 catenin. These types of junctions can be assayed according to L1, D. et al., *J. Cell Biol.*, 191(3):631-644 (2010), which is incorporated by reference.

As used herein and throughout the specification, "cell growth" refers to cell division, such that one "mother cell" divides into two "daughter cells." As used herein, "cell growth" does not refer to an increase in the actual size of the cells. Stimulation of cell growth can be assayed by plotting cell populations over time. A cell population with a steeper growth curve can said to be growing faster than a cell population with a curve not as steep. Growth curves can be compared for various treatments between the same cell types, or growth curves can be compared for different cell types with the same conditions.

The late passage NKE cells, in particular late passage normal NKE cells, of the present invention may or may not be characterized by their telomere length. As normally happens, the length of the telomeres generally shortens as cells divide. A cell will normally stop dividing when the average length of telomeres is reduced to a critical length, e.g., 4 kb. In the present invention, the average telomere length of late passage cells may be reduced to a length of as little as 2 kb and continue to grow. The average telomere length is readily determined using routine methods and techniques in the art. Thus in one embodiment, the present invention provides NKE cells, in particular normal NKE cells, capable of dividing in the culture conditions of the present invention, wherein the average telomere length of the NKE cells is shorter than the average telomere length of NKE cells that would normally not divide when placed under different or heretofore routine culture conditions. For example, the average telomere length of senescent human prostate epithelial cells (HPECs) is about 4 kb, thus when the average telomere length in HPECs is reduced to about 4 kb, the cells will normally not divide when placed in culture conditions currently considered in the art to be acceptable or even optimal for culturing prostate cells. Using the culture conditions of the present invention, however, the average telomere length of the HPECs can be reduced to a length as little as 2 kb, or even lower, and still divide and grow. Thus, the methods of the present invention are capable of generating conditionally immortalized NKE cells, in particular normal conditionally immortalized NKE cells, whereby the cells have an average telomere length that is less than the average telomere length of NKE cells that are normally capable of dividing and whereby the conditionally immortalized NKE cells are capable of still dividing in spite of their reduced telomere length. To be clear, NKE cells, in particular normal NKE cells will normally stop dividing when the average telomere length is reduced to a certain length even when placed in culture conditions currently considered in the art to be acceptable or even optimal for culturing prostate cells. The average telomere length can vary from cell type to cell type.

Such currently acceptable or optimal conditions for culturing epithelial cells generally include culturing cells in well-defined, or synthetic, serum-free medium. For examples, culturing prostate cells normally involves culturing in prostate cell-specific medium, without added serum. In addition, prostate cells, and all other NKE cells are generally cultured in the absence of feeder cells. Thus, "currently acceptable" or "currently optimal" culture conditions are culture conditions where the medium does not include serum or a serum replacement and the conditions do not include the use of feeder cells. "Currently acceptable" or "currently optimal" culture conditions may also include the use of synthetic or well-defined medium, for example the use of prostate-specific cell medium for prostate cells. Thus the methods of the present invention provide the unexpected results of being able to culture and passage NKE cells, in particular normal NKE cells, long after one would have been able to do so using currently acceptable or currently optimal conditions.

As used herein, the term "conditionally immortalized" indicates that the NKE cells have a reduced average telomere length over the average telomere length of normal senescent NKE yet are still capable of unlimited growth, provided the conditionally immortalized NKE cells, including but not limited to conditionally immortalized normal NKE cells, are maintained in the culture conditions of the present invention. When determining if a cell is conditionally immortalized, it may be necessary to compare the average telomere length of the conditionally immortalized cells with the average telomere length of non-conditionally immortalized NKE cells that would normally be senescent in vitro. The phrase "normally senescent" is used to mean a population of cells that, but for the conditions outlined herein, would a reduced capacity of dividing further in vitro and thus would not need to be passaged any further. Therefore, the invention provides methods of conditionally immortalizing NKE cells, in particular normal NKE cells, comprising culturing the NKE cells, in particular normal NKE cells, in the presence of feeder cells and a calcium-containing medium while inhibiting the activity of Rho kinase (ROCK) in the feeder cells, the NKE cells or both during culturing. As used herein, "conditionally immortalized cells" are not induced pluripotent stem cells (IPS Cells). Induced pluripotent stem cells are cells that have been reprogrammed to resemble and function like pluripotent stem cells such that the IPS cells are capable of generating a plurality of different tissues. In contrast, the conditionally immortalized NKE cells of the present invention may become less differentiated than terminally differentiated NKE cells but are able to proliferate under the conditions outlined herein. As defined herein, conditionally immortalized NKE cells of the present invention do not acquire the ability to differentiate into multiple tissue types. In one embodiment of the present invention, the conditionally immortalized cells generated by the methods described herein retain the ability to differentiate back into or form tissue from which the primary cells were isolated. In another embodiment, the conditionally immortalized NKE cells generated by the methods described herein do not retain the ability to fully differentiate back into or form tissue from which the primary cells were isolated.

The NKE cells can grow, become in need of continuous culturing and/or become conditionally immortalized in vitro without apparent change to the karyotype of the cells after any number of passages. Accordingly, the methods of the present invention comprise continuously culturing NKE cells, in particular normal NKE cells, whereby the cells' karyotype at any passage is not altered or is not substantially altered when compared to the karyotype of the same types of primary cells or early passage cells. An alteration of a cell's karyotype includes but is not limited to duplication or deletion of chromosomes or portions thereof and/or translocation of a portion of one chromosome to another. Identifying a karyotype and alterations thereof are common techniques in the art. Accordingly, one embodiment of the present invention is directed to late passage NKE cells, in particular late passage normal NKE cells wherein the late passage NKE cells have (a) an unaltered karyotype when compared to the karyotype of primary NKE cells of the same origin or (b) an unaltered karyotype when compared to the karyotype of initially thawed NKE cells of the same origin. As used herein, a late passage NKE cell is defined as an NKE cell that has gone through at least 5, 10, 15, 20, 25, 30, 35, 40, 45, 50, 55, 60, 65, 70, 75, 80, 85, 90, 95, 100, 125, 150, 175, 200, 250 or 300 passages or more.

The present invention is also directed to conditionally immortalized NKE cells, in particular conditionally immortalized normal NKE cells. In select embodiments, the conditionally immortalized NKE cells, in particular the conditionally immortalized normal NKE cells have (a) an unaltered karyotype when compared to the karyotype of primary NKE cells of the same origin or (b) an unaltered karyotype when compared to the karyotype of initially thawed NKE cells of the same origin.

The methods of the present invention comprise the use of feeder cells. The term "feeder cells" is used herein as it is in the art. Namely, feeder cells are cells that are cultured with the NKE cells of the present invention. As used herein, "culturing with NKE cells" means that the feeder cells are cultured sharing the same medium and sharing the same vessel with the NKE cells. Thus, the feeder cells need not be in direct contact with the NKE cells and, for example, can be physically separated from the NKE cells, e.g., by a porous filter, although both sets of cells are in the same vessel sharing the same medium. In one embodiment, the feeder cells are non-proliferating feeder cells. In one embodiment of the present invention, the feeder cells can be treated to inhibit proliferation of the feeders, while still keeping them alive and metabolically active. For example, feeder cells can be irradiated with gamma irradiation and/or treated with mitomycin C, which will arrest cell division but maintain the cells in a metabolically active state. Methods of treating cells to arrest cell division but maintain a metabolically active state are well-known in the art. In another embodiment, the feeder cells have not been treated to inhibit proliferation. For example, feeder cells, placed on a porous filter that prevents physical contact with the NKE cells, can be cultured with the NKE cells without the need to treat the feeder cells to inhibit their proliferation Feeder cells can be from any mammal and the animal source of the feeder cells need not be the same animal source as the NKE cells being cultured. For example feeder cells may be, but are not limited to mouse, rat, canine, feline, bovine, equine, porcine, non-human and human primate feeder cells. The types of feeder cells used are typically spleenocytes, macrophages thymocytes and/or fibroblasts. In one embodiment, the spleenocytes, macrophages thymocytes and/or fibroblasts have been treated such that they are non-proliferating. One example of a feeder cell that may be used in the methods of the present invention is a population of J2 cells. The J2 cells are a subclone of mouse fibroblasts derived from the established Swiss 3T3 cell line. In one embodiment, the J2 cells are gamma irradiated. In another embodiment, the J2 cells are treated with mitomycin C.

In another embodiment, medium conditioned with feeder cells is used in place of culturing feeder cells with the NKE cells. Preparing conditioned medium is routine in the art. Generally, preparation of conditioned medium involves culturing cells in a medium, e.g., F-medium as defined herein, for a few days and collecting this medium. The conditioned medium is often, but need not be, combined with fresh medium in a diluted fashion. Discovering the optimal dilution ratios of conditioned medium to "fresh medium" is routine, but the ratios can be from about 1:99 to about 99:1 of "conditioned medium" to "fresh medium." As used herein, "conditioned medium" is any medium where all or a percentage of the medium has been previously used in culture.

In yet another embodiment, feeder cell extract can be added to the medium in place of feeder cells themselves. Methods of preparing feeder cell extract are common and are described in Graham, J. and Sandall J., *Biochem. J.*, 182:157-164 (1979), Graham, J., *Biochem. J.*, 130:1113-1124 (1972) and Dickson, R., et al., *Proc. Nat'l Acad. Sci., U.S.A.*, 80:5335-5339 (1983) all of which are incorporated by reference herein. Discovering the optimal dilution feeder cell extract to medium is routine, but the ratios can be from about 1:99 to about 99:1 of extract to medium.

The cell culture media of the present invention can be any aqueous-based medium and can include any "classic" media such as, but not limited to DMEM (Dulbecco's Modified Essential Medium), Ham's F12 medium, Ham's F-10 medium, RPMI 1640, Eagle's Basal Medium (EBM), Eagle's Minimum Essential Medium (MEM), HEPES, Medium 199 and the like. The culture medium can also be combinations of any of the classical medium, such as but not limited to, a combination of DMEM and F12 Media.

Additional ingredients may be added to the culture medium used in the methods of the present invention. Such additional ingredients include but are not limited to, amino acids, vitamins, inorganic salts, adenine, ethanolamine, D-glucose, heparin, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, triiodothyronine (T3), thymidine and transferrin. Alternatively, insulin and transferrin may be replaced by ferric citrate or ferrous sulfate chelates. Each of these additional ingredients is commercially available.

Amino acid ingredients which may be included in the media of the present invention include but are not limited to, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine.

Vitamin that may be added include but are not limited to biotin, choline chloride, D-$Ca^{+2}$-pantothenate, folic acid, i-inositol, niacinamide, pyridoxine, riboflavin, thiamine and vitamin B12.

Inorganic salt ingredients which may be added include but are not limited to calcium salt (e.g., $CaCl_2$), $CuSO_4$, $FeSO_4$, KCl, a magnesium salt, e.g., $MgCl_2$, a manganese salt, e.g., $MnCl_2$, sodium acetate, NaCl, $NaHCO_3$, $Na_2HPO_4$, $Na_2SO_4$ and ions of the trace elements selenium, silicon, molybdenum, vanadium, nickel, tin and zinc. These trace elements may be provided in a variety of forms, preferably in the form of salts such as $Na_2SeO_3$, $Na_2SiO_3$, $(NH_4)6Mo_7O_{24}$, $NH_4VO_3$, $NiSO_4$, SnCl and ZnSO.

Additional ingredients include but are not limited to heparin, epidermal growth factor (EGF), at least one agent increasing intracellular cyclic adenosine monophosphate (cAMP) levels, and at least one fibroblast growth factor (FGF). Heparin, EGF, the cAMP-increasing agent(s) and FGF(s) may be added to the basal medium or they may be admixed in a solution of, for example, Dulbecco's Phosphate Buffered Saline (DPBS) and stored frozen until being added to basal medium to formulate the medium to be used in the methods of the present invention.

Heparin may be obtained commercially. Heparin is added to the present media primarily to stabilize the activity of the growth factor components, for example FGF. If heparin is used, it may be added to the basal medium at a concentration of about 1-500 U.S.P. units/liter. EGF is available commercially. If EGF is used, it may be added to the basal medium at a concentration of about 0.00001-10 mg/L.

A variety of agents that increase intracellular cAMP levels may be used in formulating the media of the present invention. Included are agents which induce a direct increase in intracellular cAMP levels (e.g., dibutyryl cAMP), agents which cause an increase in intracellular cAMP levels by an interaction with a cellular G-protein (e.g., cholera toxin and forskolin), agents which cause an increase in intracellular cAMP levels by acting as agonists of β-adrenergic receptors (e.g., isoproterenol) and agents which cause an increase in intracellular cAMP levels by inhibiting the activities of cAMP phosphodiesterases (e.g., isobutylmethylxanthine (IBMX) and theophylline). These cAMP-increasing agents are available commercially.

The culture medium used in the methods of the present invention comprises a calcium source. In one embodiment, the calcium source is serum or a serum replacement. In another embodiment, the calcium source is a calcium-containing salt that is added to the medium. If serum is used as a calcium source, the serum can be in a concentration (v/v) of from about 1% to about 35%. In select embodiments, the serum is at a concentration of from about 1% to about 20%, or from about 1% to about 15%, or from about 1% to about 10%, or from about 1% to about 5%. If a serum substitute or serum replacement is used as the calcium source, these can be added to the medium according to the manufacturer's suggested protocol. Examples of serum substitutes include but are not limited to commercially available substitutes such as Ultroser™ from Pall Corporation, milk or milk fractions such as but not limited to nonfat dry milk filtrate.

The range of $Ca^{+2}$ concentration used in the embodiments of the present invention can vary according to cell type. In one embodiment, the concentration of $Ca^{+2}$ in the medium used in the methods of the present invention is from 0.1 mM to 10.0 mM. In more specific embodiments, the concentration of $Ca^{+2}$ in the medium used in the methods of the present invention can be from about 0.2 mM to about 8 mM, from about 0.4 mM to about 7 mM, from about 0.5 mM to about 5 mM, from about 0.8 mM to about 4 mM, from about 1.0 mM to about 3 mM, from about 1.2 mM to about 2.8 mM, from about 1.4 mM to about 2.6 mM and from about 1.5 mM to about 2.5 mM.

The methods of the present invention comprise inhibiting rho associated coiled-coil protein kinase (ROCK) in the culture. Rho kinase belongs to the Rho GTPase family of proteins, which includes the Rho, Rac1 and Cdc42 kinases. One of the best characterized effector molecule of Rho is ROCK, which is a serine/threonine kinase that binds to the GTP-bound form of Rho. The catalytic kinase domain of ROCK, which comprises conserved motifs characteristic of serine/threonine kinases, is found at the N-terminus. ROCK proteins also have a central coiled-coil domain, which includes a Rho-binding domain (RBD). The C-terminus is made up of a pleckstrin-homology (PH) domain with an internal cysteine-rich domain. The coiled-coil domain is thought to interact with other α-helical proteins. The RBD, located within the coiled-coil domain, interacts only with activated Rho GTPases, including RhoA, RhoB, and RhoC. The pH domain is thought to interact with lipid mediators such as arachidonic acid and sphingosylphosphorylcholine, and may play a role in protein localization. Interaction of the pH domain and RBD with the kinase domain results in an auto-inhibitory loop. In addition, the kinase domain is involved in binding to RhoE, which is a negative regulator of ROCK activity.

The ROCK family currently consists of two members, ROCK1 (also known as ROKβ or p160ROCK) and ROCK2 (also known as ROKα). ROCK1 is about 1354 amino acids in length and ROCK2 is about 1388 amino acids in length. The amino acid sequences of human ROCK1 and human ROCK2 are well known. For example, the amino acid sequence of ROCK1 and ROCK2 can be found at UniProt Knowledgebase (UniProtKB) Accession Number 013464 and 075116, respectively. The nucleotide sequences of human ROCK1 and ROCK2 can be found at GenBank Accession Number NM_005406.2 and NM_004850, respectively. The nucleotide and amino acid sequences of ROCK1 and ROCK2 proteins from a variety of animals are also well-known and can be found in both the UniProt and GenBank databases.

Although both ROCK isoforms are ubiquitously expressed in tissues, they exhibit differing intensities in some tissues. For example, ROCK2 is more prevalent in brain and skeletal muscle, while ROCK1 is more abundant in liver, testes and kidney. Both isoforms are expressed in vascular smooth muscle and heart. In the resting state, both ROCK1 and ROCK2 are primarily cytosolic, but are translocated to the membrane upon Rho activation. ROCK activity is regulated by several different mechanisms, thus Rho-dependent ROCK activation is highly cell-type dependent, ranging from changes in contractility, cell permeability, migration and proliferation to apoptosis. At least 20 ROCK substrates have been identified. See Hu and Lee, Expert Opin. Ther. Targets 9:715-736 (2005) and Loirand et al, Cir. Res. 98:322-334 (2006) and Riento and Ridley, Nat. Rev. Mol. Cell. Biol. 4:446-456 (2003) all of which are incorporated by reference.

The role of ROCK in regulating apoptotic signaling is highly cell-type dependent and stimulus dependent. On the other hand, ROCK has also been associated with mediating cell-survival signals in vitro and in vivo. A ROCK-mediated pro-survival effect has been reported in epithelial cells, cancer cells and endothelial cells, as well as in other cell types. In airway epithelial cells, inhibition with Y-27632 or HA 1077 (also known as fasudil) induces membrane ruffling, loss of actin stress fibers and apoptosis (Moore et al., Am. J. Respir. Cell Mol. Biol. 30:379-387, 2004).

Rho/ROCK activation may also play a pro-survival role during oxidative stress-induced intestinal epithelial cell injury (Song et al., Am. J. Physiol. Cell Physiol. 290:C1469-1476, 2006). ROCK has also been associated with pro-survival events in thyroid cancer cells (Zhong et al., Endocrinology 144:3852-3859, 2003), glioma cells (Rattan et al, J. Neurosci. Res. 83:243-255, 2006), human umbilical vein endothelial cells (Li et al., J. Biol. Chem. 277:15309-15316, 2002), hepatic stelate cells (Ikeda et al., Am. J. Physiol. Gastrointest. Liver Physiol. 285:G880-886, 2003) and human neuroblastoma cells (De Sarno et al., Brain Res. 1041: 112-115, 2005). Evidence of ROCK playing a pro-survival role has also been reported in vivo, for example in vascular smooth muscle cells (Shibata et al, Circulation 103:284-289, 2001) and spinal motor neurons (Kobayashi et al, J. Neurosci. 24:3480-3488, 2004).

Figure 23:
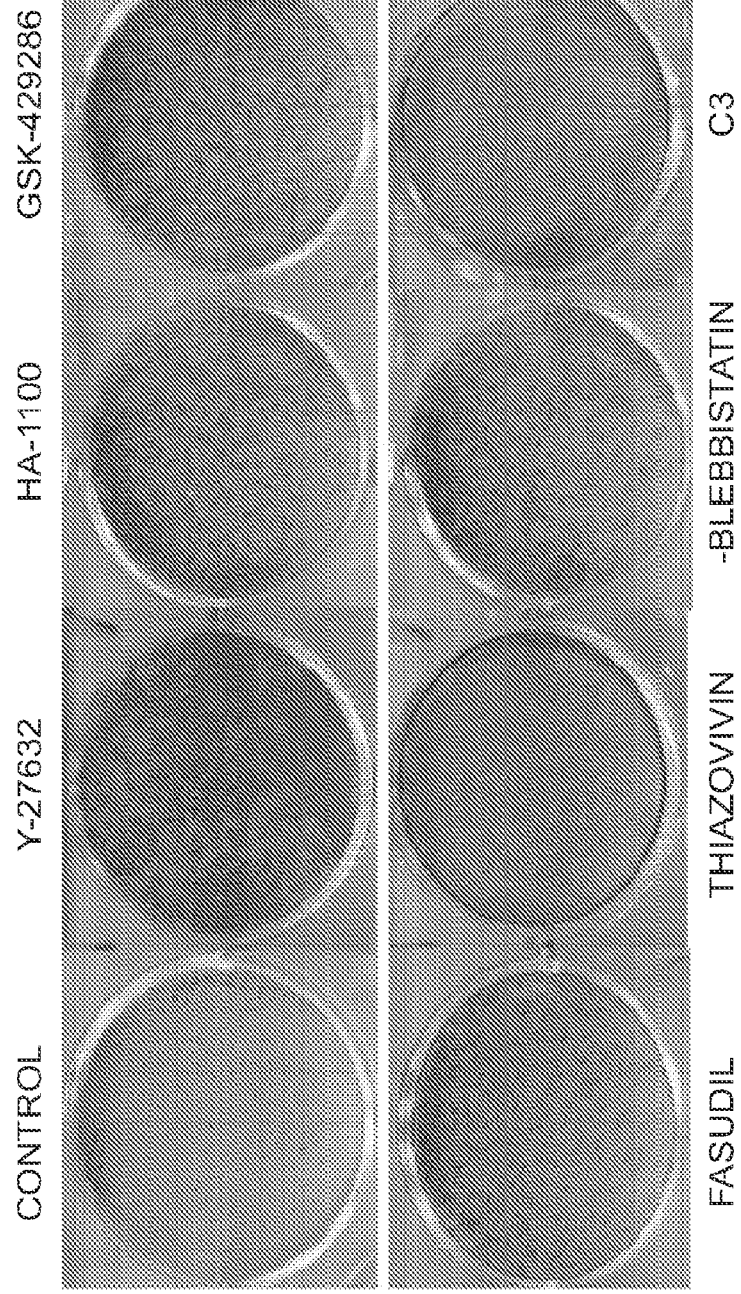
FIG. 23 depicts that inhibition of the Rho-Rock-Myosin pathway prevents cells from terminally differentiating, allowing the cells to proliferate in serum-containing medium. Normally, serum-containing medium induces terminal differentiation of primary epithelial cells and, in turn, causes senescence in culture. Approximately 5000 human prostate cells were plated in 6-well plates in F medium with addition of Rock inhibnitors Y-27632 (5 μM), HA-1100 (20 μM), GSK429286 (0.1 μM), Fasudil (30 μM), a Rho inhibitor (C3 transferase, 2 μg/ml), or a Mysin inihibitor (-Blebbistatin, 5 μM). Eight days later, cells were fixed and stained with 0.05% Crystal Violet. The data suggest that inhibition of Rho-Rock-Myosin pathway with inhibitors was able to suppress cell differentiation by serum.
Figure 24:
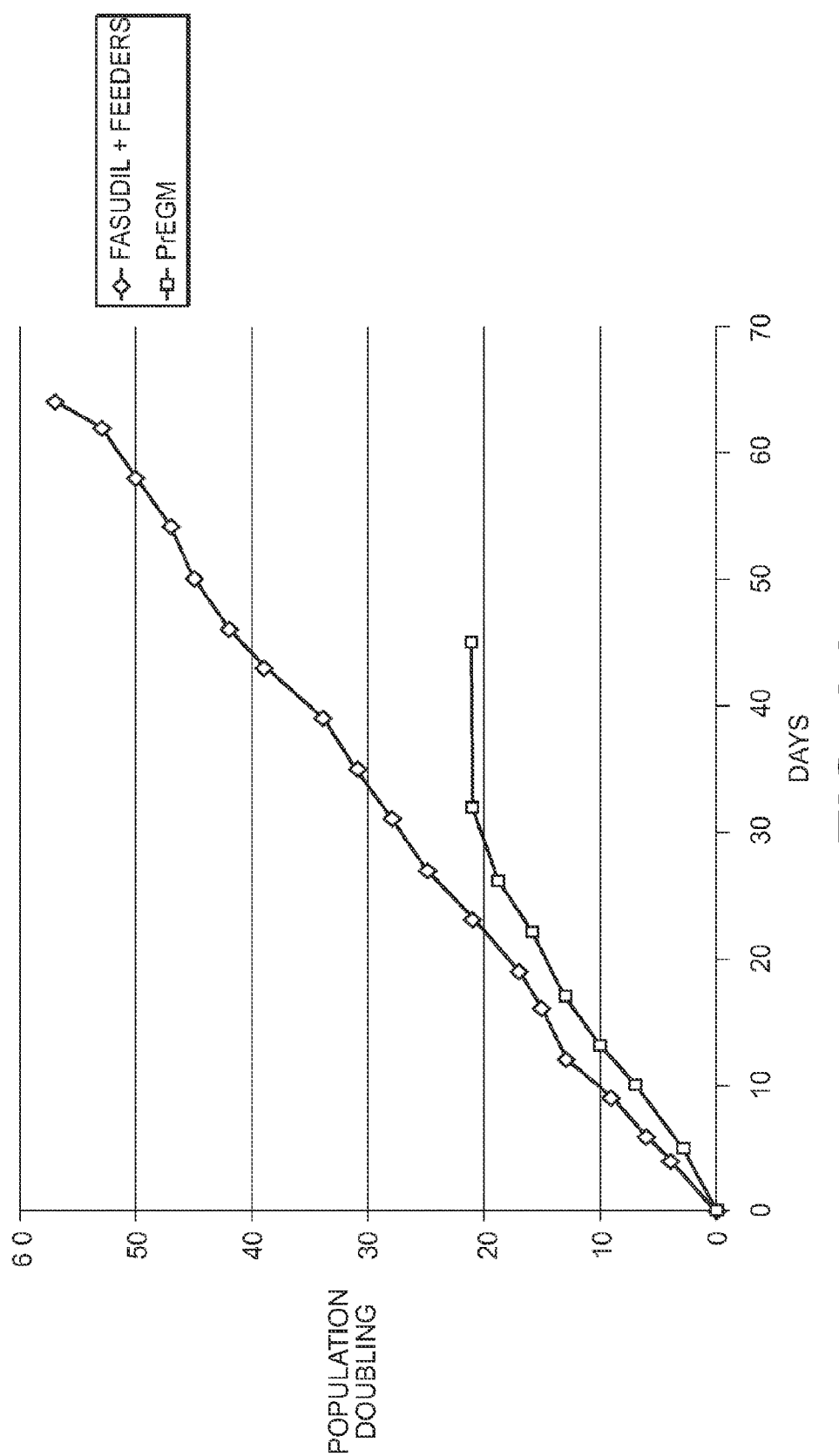
FIG. 24 depicts in vitro growth curves of human primary prostate cells in synthetic medium compared to prostate cells grown under the conditions described herein. PrEGM is a synthetic commercial prostate epithelial cell growth medium; Feeders are J2 mouse fibroblasts that have been irradiated or treated with mitomycin C; the ROCK inhibitor was Fasudil at a concentration of 30 μM. The y-axis is population doublings and the x-axis is number of days.

As used herein, inhibiting ROCK can mean to reduce the activity, function or expression of at least one of ROCK1 or ROCK2. The activity, function or expression may be completely suppressed, i.e., no activity, function or expression, or the activity, function or expression may simply be lower in treated versus untreated cells. In general, ROCK phosphorylates LIM kinase and myosin light chain (MLC) phosphatase after being activated through binding of GTP-bound Rho. One embodiment of the present invention thus involves blocking the upstream pathway of ROCK1 and/or ROCK2, for example GTP-bound Rho, such that ROCK1 and/or ROCK2 is not activated or its activity is reduced over untreated cells. Other upstream effectors include but are not limited to, integrins, growth factor receptors, including but not limited to, TGF-beta and EGFR, cadherins, G protein coupled receptors and the like. Another embodiment of the present invention thus involves blocking the activity, function or expression of downstream effector molecules of activated ROCK1 and/or ROCK2 such that ROCK1 and/or ROCK2 can not propagate any signal or can only propagate a reduced signal over untreated cells. Downstream effectors include but are not limited to, Myosin phosphatase-targeting protein (MYPT), vimentin, LIMK, Myosin light chain kinase, NHE1, cofilin, Myosin II and the like. For example, both C3 transferase, a ROCK upstream inhibitor that inhibits the activity of Rho, and blebbistatin, a ROCK downstream inhibitor that inhibits the activity of myosin II, when used in the culture conditions described herein in place of a ROCK inhibitor, affected the cells in such a manner as to allow the cells to bypass differentiation and allow proliferation in vitro (FIG. 23). Upstream or downstream inhibition of ROCK, in place of direct ROCK inhibition and in conjunction with the other culture conditions described and required herein, may or may not generate conditionally immortalized NKE cells.

The methods of the present invention comprise inhibiting ROCK while culturing the NKE cells, in particular normal NKE cells. In one embodiment, inhibiting ROCK is accomplished by addition of a ROCK inhibitor to the culture medium. In this embodiment where a ROCK inhibitor is added to culture medium, it is possible that the ROCK inhibitor may also be having an effect on the feeder cells in addition to the NKE cells.

Figure 11:
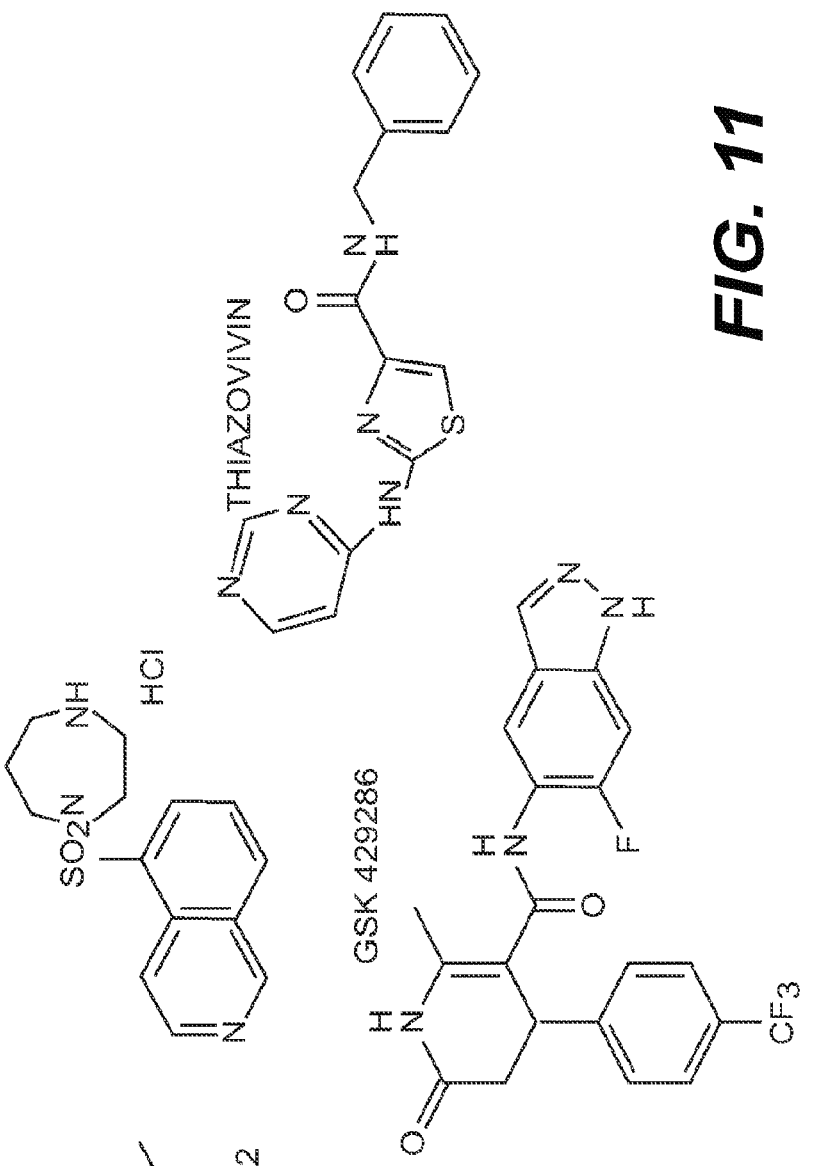
FIG. 11 depicts the chemical structure of a few representative ROCK inhibitors.

Examples of ROCK inhibitors include but are not limited to Y-27632, HA1100, HA1077, Thiazovivin and GSK429286, the structures of which are depicted in FIG. 11. These compounds are well known and commercially available. Additional small molecule Rho kinase inhibitors include but are not limited to those described in PCT Publication Nos. WO 03/059913, WO 03/064397, WO 05/003101, WO 04/112719, WO 03/062225 and WO 03/062227, and described in U.S. Pat. Nos. 7,217,722 and 7,199,147, and U.S. Patent Application Publication Nos. 2003/0220357, 2006/0241127, 2005/0182040 and 2005/0197328, the contents of all of which are incorporated by reference.

Another way of inhibiting ROCK kinase would be through the use of RNA interference (RNAi). RNAi techniques are well known and rely of double-stranded RNA (dsRNA), where one stand of the dsRNA corresponds to the coding strand of the mRNA that codes for ROCK1, and the other strand is complementary to the first strand. The requirements of optimal RNAi species for a given nucleotide sequence are well-known or can be readily ascertained given the state of the art. For example, it is known that optimal dsRNA is about 20-25 nt in length, with a 2 base overhand on the 3' end of each strand of the dsRNA, often referred to as short interfering RNAs (siRNA). Of course, other well-known configurations such as short hairpin RNA (shRNA) may also work. shRNAs are one continuous RNA strand where a portion is self-complementary such that the molecule is double-stranded in at least one portion. It is believed that the cell processed shRNA into siRNA. The term RNAi molecule, as used herein, is any double stranded double-stranded RNA (dsRNA), where one stand of the dsRNA corresponds to the coding strand of the mRNA that codes for the target gene to be silenced, and the other strand is complementary to the first strand.

Accordingly, one embodiment of the present invention involves the use of at least one RNAi molecule and/or at least one antisense molecule, to inhibit the activity of ROCK. In one specific embodiment, the RNAi molecule and/or antisense molecule is specific towards ROCK1. In another embodiment, the RNAi molecule or antisense molecule is specific towards ROCK2. In yet another embodiment, the RNAi molecule and/or antisense molecule is specific towards both ROCK1 and ROCK2. In still another embodiment, at least two RNAi molecules and/or antisense molecules are used, where one is specific towards ROCK1 and the other is specific towards ROCK2.

The RNAi molecules and/or antisense molecules may be part of the cell culture by simply soaking the cells with the naked RNAi molecules and/or antisense molecules as has been reported Clemens, J. C., et al., *PNAS,* 97(12):6499-6503 (2000), which is incorporated by reference. The RNAi molecules and/or antisense molecules may also be part of a complex, such as a liposomal complex that can be used to insert RNAi molecules or antisense/molecules into the cells.

Liposomes fall into two broad classes. Cationic liposomes are positively charged liposomes which interact with the negatively charged dsRNA molecules to form a stable complex. The positively charged dsRNA/liposome complex binds to the negatively charged cell surface and is internalized in an endosome. Due to the acidic pH within the endosome, the liposomes are ruptured, releasing their contents into the cell cytoplasm (Wang et at., Biochem. Biophys. Res. Commun., 1987, 147, 980-985).

Liposomes that are pH-sensitive or negatively-charged entrap dsRNA rather than complex with it. Since both the dsRNA and the lipid are similarly charged, repulsion rather than complex formation occurs. The dsRNA is thus entrapped in the aqueous interior of these liposomes. pH-sensitive liposomes have been used, for example, to deliver dsRNA encoding the thymidine kinase gene to cell monolayers in culture (Zhou et al., Journal of Controlled Release, 1992, 19, 269-274). One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol. Liposomes that include nucleic acids have been described, for example, in WO 96/40062, U.S. Pat. No. 5,264,221, U.S. Pat. No. 5,665,710 and Love et al., WO 97/04787 all of which are incorporated by reference.

Another type of liposome, a transfersome, is a highly deformable lipid aggregate which is attractive for drug delivery vehicles. (Cevc et al., 1998, Biochim Biophys Acta. 1368 (2): 201-15.) Transfersomes may be described as lipid droplets which are so highly deformable that they can penetrate through pores which are smaller than the droplet. Transfersomes are adaptable to the environment in which they are used, for example, they are shape adaptive, self-repairing, frequently reach their targets without fragmenting, and often self-loading. Transfersomes can be made, for example, by adding surface edge-activators, usually surfactants, to a standard liposomal composition.

Another way ROCK1 and/or ROCK2 RNAi can gain access to the cells in the methods of the present invention is through the use of DNA expression vectors that encode the RNAi molecules and/or antisense molecules. Certain embodiments can utilize only one vector, for example when the RNAi molecule is a shRNA, or when opposing promoters are placed on either side there of the coding sequence for the RNAi molecule. Thus "inhibiting the activity of ROCK" includes the use of DNA that, when transcribed, can block the activity, function or production of ROCK. The liposomal delivery systems described above are one way in which the DNA encoding an RNAi and/or antisense can enter the cell.

Alternatively, the DNA encoding an RNAi and/or antisense can be prepared in a viral vector system that has the capability of entering into cells. These are well-known in the art and include Madzak et al., J. Gen. Virol., 73: 1533-36 (1992) (papovavirus SV40); Berkner et al., Curr. Top. Microbiol. Immunol., 158: 39-61 (1992) (adenovirus); Moss et al., Curr. Top. Microbiol. Immunol., 158: 25-38 (1992) (vaccinia virus); Muzyczka, Curr. Top. Microbiol. Immunol., 158: 97-123 (1992) (adeno-associated virus); Margulskee, Curr. Top. Microbiol. Immunol., 158: 67-93 (1992) (herpes simplex virus (ISV) and Epstein-Barr virus (HBV)); Miller, Curr. Top. Microbiol. Immunol., 158: 1-24 (1992) (retrovirus); Brandyopadhyay et al., Mol. Cell. Biol., 4: 749-754 (1984) (retrovirus); Miller et al., Nature, 357: 455-450 (1992) (retrovirus); Anderson, Science, 256: 808-813 (1992) (retrovirus); C. Hofmann et al., Proc. Natl. Acad. Sci. USA, 1995; 92, pp. 10099-10103 (baculovirus).

In another embodiment, ROCK1 and/or 2 are inhibited using genetic manipulation techniques, such as, but not limited to, transgenic techniques involving either knockout or dominant negative constructs. Such constructs are disclosed in Khyrul, W., et al., J. Biol. Chem., 279(52):54131-54139 (2004), which is incorporated by reference herein.

As mentioned above, one embodiment of blocking ROCK would be to individually or collectively block or inhibit the upstream or downstream effectors molecules of ROCK using any of the methods described herein, such as but not limited to small molecule inhibitors, RNAi techniques, antisense techniques and/or genetic manipulation. Accordingly, any upstream effectors that could be inhibited include but are not limited to, integrins, growth factor receptors, including but not limited to, TGF-beta and EGFR, cadherins, G protein coupled receptors and the like. In addition, any downstream effectors that could be inhibited include but are not limited to, vimentin, LIMK, Myosin light chain kinase, NHE1, cofilin and the like.

After culturing in the conditions of the present invention, the cells may be removed from these conditions and placed in a cell culture environment where the environment is absent feeder cells, absent a calcium source and/or absent a ROCK inhibitor. Any combination of one, two or three of: the feeder cells, the calcium source and the ROCK inhibitor may be absent in the subsequent environment. As used herein, a "subsequent environment" when used in connection with a cell culture environment is a cell culture environment in which at least one of the feeder cells, the calcium source and the ROCK inhibitor is absent. In one embodiment, the ROCK inhibitor, the calcium source or the feeder cells are absent in the subsequent environment. In another embodiment, the feeder cells and ROCK inhibitor are absent from the subsequent environment. In another embodiment, the feeder cells and calcium source are absent from the subsequent environment. In another embodiment, the calcium source and ROCK inhibitor are absent from the subsequent environment. In another embodiment, the feeder cells, ROCK inhibitor and calcium source are absent from the subsequent environment.

Figure 20:
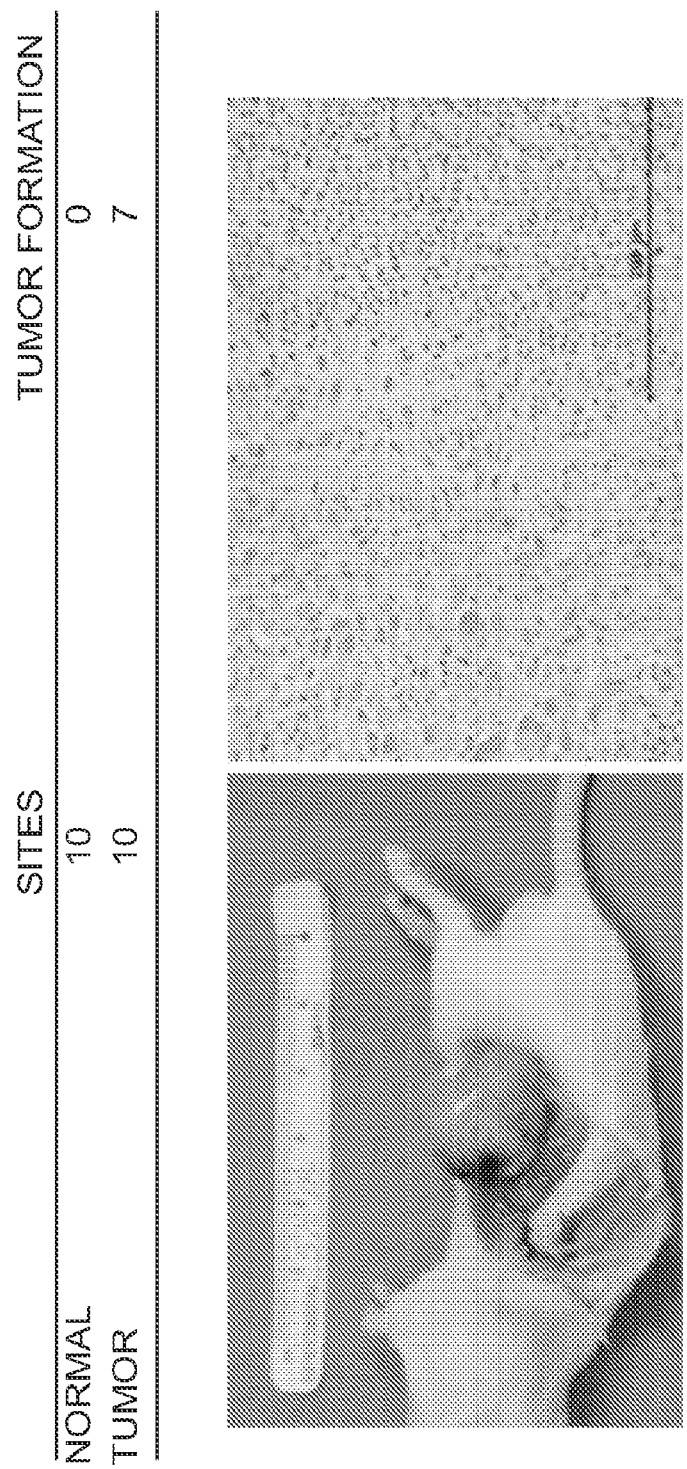
FIG. 20 depicts only prostate tumor cells being tumorigenic in vivo. $1 \times 10^6$ exponentially growing normal or tumor prostate cells from the same patient were trypsinized, dispersed into single cells, and suspended in 200 μl of Matrigel HC (BD Biosciences, Bedford, Mass.). The Matrigel suspended cells were injected subcutaneously into the left and right flank of 6 week old male ICR SCID mice (Taconic, Germantown, N.Y.), 5 mice for each cell type, a total of 10 sites for each cell type. The growth of xenografts was measured weekly with calipers. The prostate cancer cells induced tumors at 7 of 10 sites within 8 weeks. The normal prostate cells, however, did not induce any tumors (0/10 sites). The right panel shows tumor histology.
Figure 21:
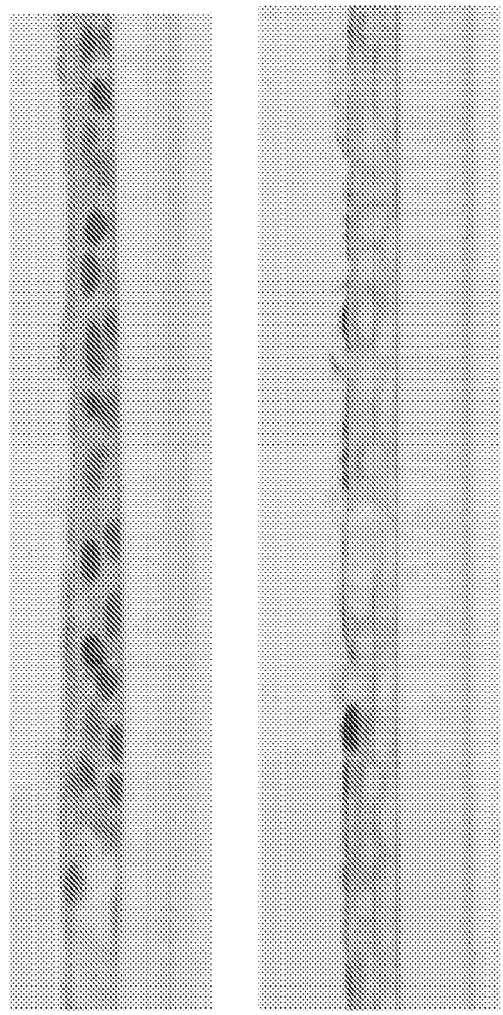
FIG. 21 depicts that normal tracheal-bronchial cells form cilia at the air-liquid interface (ALI) in culture. A representative cell line generated from primary tracheal-bronchial epithelial cells was plated onto Snapwellsin ALI medium and Vertex medium. Upon confluence, usually beginning at days 5-7, cells were maintained at an ALI. The apical surface was washed with PBS, and medium was replaced only in the basal compartment three times per week. At day 28, the ALI cultures were fixed in formaldehyde, processed and embedded in paraffin. After sectioning, the cells were stained with either hematoxylin and eosin (H&E) (upper panel) or alcian blue-periodic acid-Schiff (ABPAS) (lower panel) stain. The sparse ciliated cells and mucous secretory cells are photographed.

In one embodiment, the subsequent environment to the NKE cells, the late passage NKE cells and/or the conditionally immortalized NKE cells is an environment that can promote differentiation and/or does not allow for indefinite proliferation of the NKE cells, the late passage NKE cells and/or the conditionally immortalized NKE cells. The subsequent environment may be an in vivo environment that is similar or identical to the organ from which the cells were originally derived, i.e., an autologous implant. For example, hepatocytes that have been cultured according to the methods of the present invention can be reintroduced into the liver of the subject from which the cells were initially biopsied or isolated. FIG. 20 shows human prostate tumor cells were harvested and subjected to the culture conditions described herein to create a conditionally immortalized prostate cancer cell line. The conditionally immortalized prostate cancer cells were placed into SCID mice, i.e., a subsequent in vivo environment, and these conditionally immortalized prostate cancer cells were able to generate new tumors in the mice.

The subsequent environment may be an in vitro environment that is that more closely resembles the biochemical or physiological properties of the organ from which the cells were originally derived once placed in this subsequent environment. The subsequent environment may also be a "synthetic environment" such that factors known to promote differentiation in vitro are added to the cell culture. For example, late passage liver epithelial cells, once placed in a subsequent environment that is designed to promote differentiation of the cells, may begin to form clusters and/or express proteins that resemble mature liver epithelial cells.

In one embodiment, NKE cells, the late passage NKE cells and or the conditionally immortalized NKE cells are placed into a subsequent environment that is specific to stimulate differentiation of cells into the cells of the organ from which the cells were originally derived. For example, conditionally immortalized prostate epithelial cells can be removed from the conditions of the present invention and placed into culture conditions designed to promote differentiation of prostate cells. Various environments for culturing epithelial cells are detailed in *Culture of Epithelial Cells* (Ian Freshney and Mary G. Freshney, Eds. Wiley-Liss, Inc.)($2^{nd}$ Ed. 2002), which is incorporated by reference.

Alternatively, the cells can be seeded in a subsequent environment into or onto a natural or synthetic three-dimensional cell culture surfaces. One non-limiting example of a three-dimensional surface is a Matrigel®-coated culture surface. Other three dimensional culture environments include surfaces comprising collagen gel and/or a synthetic biopolymeric material in any configuration, such as but not limited to a hydrogel. Of course, a variety of three dimensional culture surfaces may be used simultaneously with the methods the present invention. If a three-dimensional culture environment is used, the feeder cells may or may not be used as well. These three-dimensional cell culture surface environments may or may not promote differentiation.

In one embodiment, NKE cells, the late passage NKE cells and or the conditionally immortalized NKE cells can be genetically modified to express a protein of interest. The genetic modification of the cells would not be a modification designed to immortalize the cells, such as the insertion of a viral protein. Rather, the genetic modification of the cells would be designed to, for example, insert a transgene that codes for a protein. For example, hepatocytes can be isolated and expanded using the cell culture methods of the present invention. These cells can subsequently be manipulated and a transgene coding for Factor VIII can be inserted in the genome of the cells, such that the cells can produce Factor VIII. These cells can then be placed in a subsequent environment, such as an autologous implant into a subject, such that the cells will produce Factor VIII. As another example, lung epithelial cells could be isolated from subject suffering from cystic fibrosis. These cells could then be expanded using the cell culture methods of the present invention and a transgene coding for the cystic fibrosis transmembrane conductance regulator could be inserted into these cells in vitro. The genetically modified NKE cells could then be reconstituted onto denuded bronchial epithelium to restore normal function. It is estimated that only 10% of the epithelial surface would need to be replaced in order to restore normal function. The formation of a pseudostratifed, columnar epithelium with ciliated cells would be indicative of the reformation of normal tissue. See Fulcher M. L. et al., Well-Differentiated Human Airway Epithelial Cell Cultures. Methods in Molecular Medicine, 107: Human Cell Culture Protocols, pp 183-206, Second Edition Edited by: J. Picot. Humana Press Inc., Totowa, N.J., which is incorporated by reference.

The methods by which the transgenes are introduced into the cells are standard methods known from the literature for in vitro transfer of DNA into mammalian cells, such as electroporation; calcium phosphate precipitation or methods based on receptor-mediated endocytosis, disclosed in WO 93/07283, which is incorporated by reference. Other methods and materials for inserting a gene of interest into cells are disclosed in Sambrook et al., Molecular Cloning: A Laboratory Manual, Cold Springs Harbor Laboratory Press, Third Edition (2001), which is incorporated by reference.

A wide variety of genes of interest can be expressed in the NKE cells, the late passage NKE cells and or the conditionally immortalized NKE cells. These genes of interest include, but are not limited to, sequences encoding toxins, clotting factors, enzymes, prodrug converting enzymes, antigens which stimulate immune responses, tumor necrosis factors, cytokines, and various proteins with therapeutic applications (e.g., growth hormones and regulatory factors).

After transfecting the NKE cells, the late passage NKE cells and/or the conditionally immortalized NKE cells of the present invention, these cells that were successfully transfected can be selected for using a markers that are well known in the art. After selection of the successfully transfected cells, the genetically modified NKE cells, the late passage NKE cells and/or the conditionally immortalized NKE cells of the present invention can be cultured using the cell culture techniques of the present invention to produce a population of genetically modified NKE cells, late passage NKE cells and/or conditionally immortalized NKE cells. These cells can subsequently be collected and placed into a subsequent environment as described above, including but not limited to being placed back into the subject, i.e., an autologous implant.

The present invention is also directed to methods of identifying candidate treatments for a subject in need of treatments for which the subject has a condition marked by the presence of abnormal or diseased NKE cells. Such conditions marked by the presence of abnormal or diseased NKE cells include but are not limited to neoplasias, a hyperplasias or malignant tumors or benign tumors. The methods comprising obtaining a sample of the abnormal NKE cells from the subject and culturing the abnormal NKE cells according to any of the culture methods of the present invention to produce an in vitro population of abnormal NKE cells. For example, circulating tumor cells (CTCs) may be isolated from the organism's circulation, and the methods of the present invention may be utilized to obtain a sufficient number of cells for further analysis, such as but not limited to, phenotypically or genetically characterizing the cells. One method of isolating CTCs is disclosed herein, but the invention is not limited to any method by which CTCs are isolated. In the past, CTCs were isolated but could not be kept in culture for any significant time to permit study and analysis. The present invention, however, solves this problem by allowing a minimal number of CTCs, even a single cell, to be isolated and plated. The plated CTC(s) are/is then subjected to the inventive methods of the present invention to establish and maintain enough cells to permit subsequent genetic, functional and/or phenotypic analysis. Indeed, once a sufficient number of abnormal or diseased NKE cells are obtained, regardless of their source, these cells can also be assayed to determine a response profile, which can be used to identify a candidate treatment for the subject.

A response profile, as used herein, is a collection of one or more data points that would indicate, e.g., to a clinician, the likelihood that a particular treatment will produce a desired response in the abnormal NKE cells if they were in an in vivo setting. A "response" as used in connection with a response profile may or may not be either cell death by any means (necrosis, toxicity, apoptosis etc) or a reduction of the growth rate of the abnormal cells. The response profile need not predict a response with 100% accuracy. A response profile can be a single data point or it can be a collection of data.

Any method can be used to identify or determine the response profile of a given population of abnormal NKE cells. For example, the response profile may be assessed by sequencing at least part of the DNA or RNA that is isolated from the abnormal cells. This may be particularly useful when it is suspected that a virus, e.g., human papilloma virus (HPV), human immunodeficiency virus (HIV) may be causing the abnormal condition. It is not necessary that all of the DNA/RNA be sequenced to provide at least one data point for the response profile. For example, using well-known techniques involving polymerase chain reaction (PCR), it would currently be a matter of simple procedure to use PCR primers with sequences specific for the DNA/RNA suspected of being present, e.g., HPV or HIV, in a PCR reaction to determine if a product is made. If no detectable product is generated after the PCR reaction using specific primers, it may be possible to conclude that the portion of the virus for which the PCR primers are specific may not be present. Likewise, determining the absence of a particular DNA/RNA sequence could also be a data point in a response profile. In this manner, the DNA or RNA is "sequenced" for the purposes of the present invention, although the precise sequence is not determined for the entire DNA/RNA sequence isolated from the cells. Thus, "sequencing" as used herein may or may not result in generating the entire nucleotide sequence of the isolated DNA/RNA. Other methods can also be used to determine the sequence of the isolated DNA/RNA such as, but not limited to Southern blots, Northern blots, RT-PCR, automated sequencing and the like. Methods of sequencing DNA/RNA are well known in the art and need not be repeated herein.

Similarly, the response profile may be assessed by identifying the presence or absence of at least a portion of one mRNA that may be produced in the abnormal NKE cells in vitro. Like determining the sequence of the DNA/RNA above, the precise sequence of the mRNA need not be determined for the entire mRNA isolated from the cells. Methods that can also be used to determine the presence or absence of the sequence of the isolated mRNA include but are not limited to Northern blots, RT-PCR, automated sequencing and the like. Methods of identifying the presence or absence of the at least one mRNA are well known in the art and need not be repeated herein.

Similarly, the response profile may be assessed by identifying the presence or absence of at least a portion of one protein that may be produced in the abnormal NKE cells in vitro. Like determining the sequence of the DNA/RNA above, the precise amino acid sequence of the present or absent protein need not be determined for the entire protein. Methods that can also be used to determine the presence or absence of the sequence of the isolated protein include but are not limited to Western blots, immunohistochemical methods, ELISA methods, and the like. Methods of identifying the presence or absence of the at least one protein are well known in the art and need not be repeated herein. The presence or absence of a protein, e.g., a receptor, may indicate that the cells are susceptible to a particular treatment that may, for example, result in cell death.

The response profile may be assessed by subjecting the abnormal NKE cells in vitro to a chemotherapeutic agent and determining the response of the cells to the chemotherapeutic agent. As used herein, a chemotherapeutic agent is not limited to traditional cancer treatments but is used to indicate a therapeutic treatment of any kind using a chemical entity. In one embodiment, the response to the therapeutic agent can be assessed by determining the therapeutic index of the agent on the cells. Determining the therapeutic index is common in the art and is simply the ratio of the $LD_{50}/EC_{50}$, with the $LD_{50}$ representing the median lethal dose and the $EC_{50}$ representing the half maximal dose of the agent on the cells. Other methods to assess a response to the agent include but are not limited to determining dose response curves, cell survival curves and the like. In one embodiment, the agent that is used to determine the response of the abnormal NKE cells to the agent can be the same or a different agent that is later administered to the subject.

The present invention is also directed to methods of identifying an abnormal non-keratinocyte epithelial (NKE) cell in a subject. These methods comprise culturing at least one candidate abnormal NKE cell isolated from the subject according to the cell culture methods of the present invention. Once the NKE cells, the late passage NKE cells and or the conditionally immortalized NKE cells have been expanded, a tissue origin profile can be determined for the cells to determine the likely tissue of origin of the candidate abnormal NKE cells. At least one feature of the NKE cells, the late passage NKE cells and or the conditionally immortalized NKE cells can be compared to the same feature of normal NKE cells that are obtained from the same tissue as that of the determined tissue origin profile of the candidate abnormal NKE cells. Any difference between abnormal or diseased cells and normal cells can be used, including but not limited to, cell growth characteristics, for example, colony formation on a cell surface, Matrigel™ or other three-dimensional surface. Other means of determining differences between diseased and normal cells include, but are not limited to, assessing the proteomic profile of the cells, assessing the metabolomic profile of the cells, assessing the genomic profile, and/or using other biological assays that will highlight a difference between diseased or abnormal cells and normal cells. A detected difference in the candidate abnormal NKE cells and the normal NKE cells would indicate that the candidate abnormal NKE cells are abnormal compared to normal NKE cells.

The same methods that are used to assess a response profile can be used to assess a tissue origin profile. For example, the candidate abnormal cells can be assayed for mRNA transcript production, protein expression and tissue origin can also be assessed visually through histological evaluation. Methods of assessing a tissue origin profile also include immunohistochemical staining. Once a likely tissue of origin has been established for the candidate abnormal cells, the cells can be assayed for at least one feature of normal cells from the same tissue. For example, if a candidate abnormal cell has been identified as originating from mammary tissue, these cells can be assayed for the BRCA1 and/or BRCA2 mutation, overexpression of the HER-2/neu growth factor receptor and the like. If the candidate abnormal cell has the BRCA1 mutation, the cell can then be confirmed as being an abnormal mammary cell. The invention is not limited to the types of assays used to identify the tissue of origin; nor is the invention limited to the types of assays used to determine differences in normal and potentially abnormal cells. The cell culture methods of the present invention enable the identification of these cells by providing methods for expanding the isolated cells.

The present invention is also directed to methods of monitoring the progression of a disease or treatment of a disease in a subject. As used herein, the phrase "monitor the progression" is used to indicate that the abnormal condition in the subject is being periodically checked to determine if an abnormal condition is progressing (worsening), regressing (improving) or remaining static (no detectable change) in the individual by assaying NKE cells and/or their cellular contents for various markers of progression or regression. The methods of monitoring may be used in conjunction with other monitoring methods or treatment regimens for an abnormal condition and to monitor the efficacy of these treatments. Thus, "monitor the progression" is also intended to indicate assessing the efficacy of a treatment regimen by periodically assaying NKE cells and/or their cellular contents for various markers of progression or regression and correlating any differences in the subject over time with the progression, regression or stasis of the abnormal condition. For example, the methods of the present invention may be used to monitor a subject during or after mastectomy. In particular, the methods may be used to monitor patients that have had a successful mastectomy, such that the methods can be used to isolate CTCs to culture and generate enough CTCs in vitro to perform various analyses on the patient's CTCs to determine, if for example, a followup mammogram or body scan would be necessary. The methods of monitoring can also be used to determine a suitable follow up therapeutic regimen, after an initial treatment. For example, after an initial treatment NKE cells can be biopsied or isolated and the culture methods can be used to generate enough cells in vitro to determine if the genetic makeup or phenotype of the remaining abnormal cells is sufficiently different enough to warrant a new therapy. Thus, in one embodiment, the present invention provides methods of individualizing a therapeutic regimen. Monitoring may also include assessing the levels of a specific marker on NKE cells at two time points from which a sample is taken, or it may include more time points, where any of the levels the marker at one particular time point from a given subject may be compared with the levels of biomarker in the same subject, respectively, at one or more other time points.

The methods comprising obtaining a sample of the abnormal NKE cells from the subject and culturing the abnormal NKE cells according to any of the culture methods of the present invention to produce an in vitro population of abnormal NKE cells.

the phrase "monitor the progression" the levels of AIB1-Δ4 peptide in the subject using the methods of the present invention.

The present invention also provides kits for culturing NKE cells and/or generating conditionally immortalized NKE cells. The kits can include culture vessels, culture media in wet or dry form and/or individual media components such as serum or some other calcium source. The kit may or may not include frozen feeder cells, other chemicals, such as trypsin, for passaging cells, etc.

EXAMPLES

Example 1

Harvesting and Culturing of Primary Human Prostate Cells (HPECs)

Normal human prostate tissues were collected with the informed consent of the patients or parents. A primary prostate cell suspension was prepared according to well-established procedures using trypsin. Briefly, prostate tissue was harvested digested with trypsin. The cells were then suspended in DMEM containing 10% serum (to neutralize the trypsin) and immediately centrifuged to isolate the pelleted cells. Such method of routine isolation and culturing of prostate epithelial cells are found in *Culture of Epithelial Cells* (Ian Freshney and Mary G. Freshney, Eds. Wiley-Liss, Inc.) ($2^{nd}$ Ed. 2002), which is incorporated by reference.

After spinning, the pellet was removed and disbursed and plated in "F medium." F medium is prepared by mixing F-12 and DMEM (Gibco) in a 3:1 (v/v) ratio with 5% fetal bovine serum, 0.4 μg/ml hydrocortisone, 5 μg/ml insulin, 8.4 ng/ml cholera toxin, 10 ng/ml epithelial growth factor (EGF), 24 μg/ml adenine, 100 U/ml penicillin and 100 μg/ml streptomycin. A ROCK inhibitor, Y027632 was added to the F medium at a concentration of about 10 μM.

The cells were plated in the presence of non-proliferating feeder cells. In this particular case, the feeder cells were the well-known mouse fibroblast feeder J2 cells, a subclone of Swiss 3T3 cells, that had been gamma irradiated. Gamma irradiation or treatment with mitomycin C treatment renders these cells incapable of proliferating.

The cells were cultured in standard cell culture vessels under normal cells culture conditions, 37° C. at 5% $CO_2$ and normal atmospheric pressure. Medium was changed every 2-3 days depending upon growth rate.

After the cells reached confluence, the cells were harvested and passaged using standard cell culturing techniques as described in Chapman, S. et al., *J. Clin. Invest.*, 120(7):2619-2626 (2010), which is incorporated by reference.

Figure 3A:
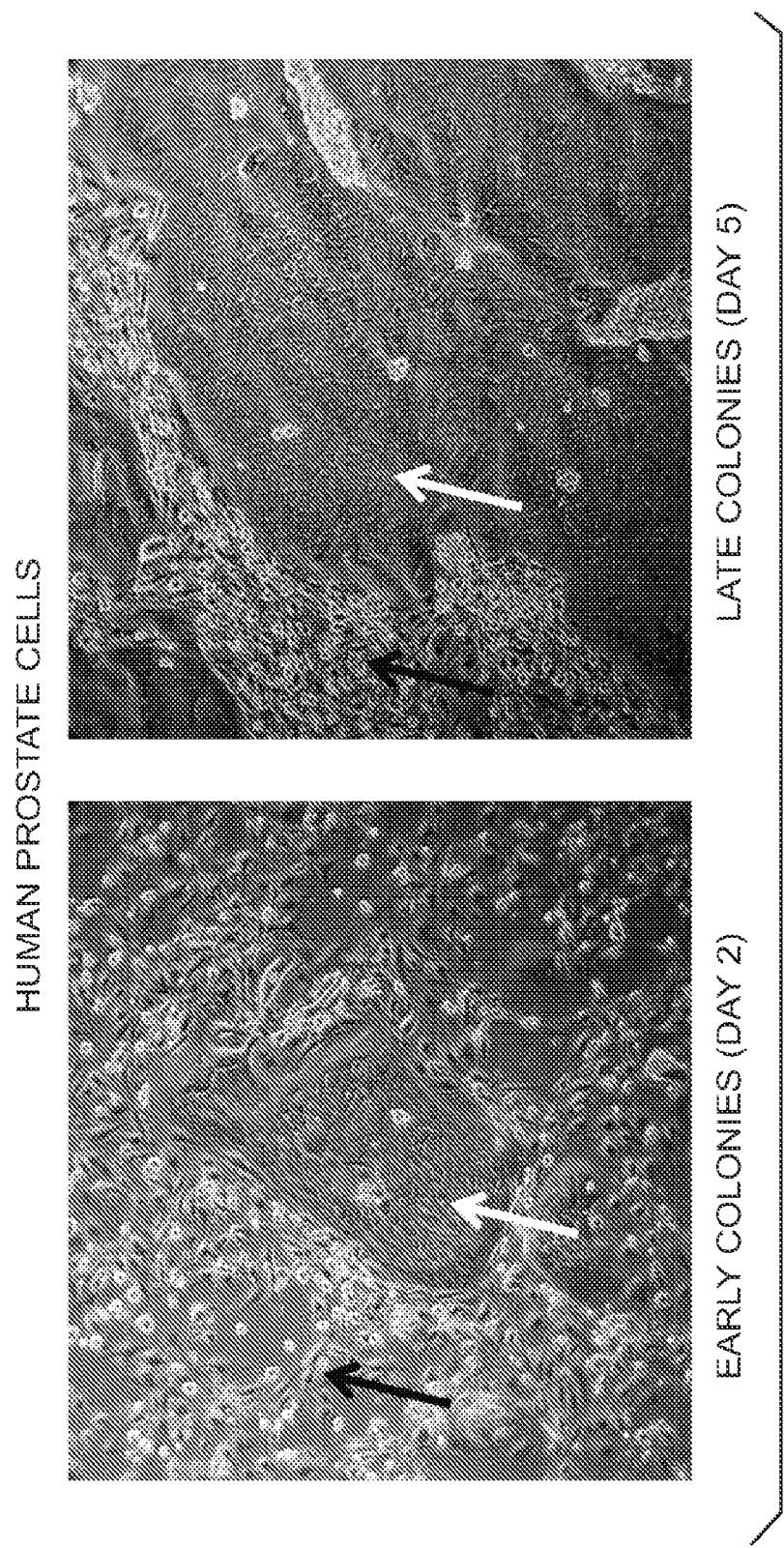
FIG. 3 depicts early passage normal human prostate (A) and normal human mammary (B) epithelial cells grown using the methods and culture conditions disclosed herein. All cells were grown in F medium supplemented with 5% fetal bovine serum and in the presence of the ROCK inhibitor Y27632 at a concentration of 10 μM. The arrows in the center of each figure are highlighting the epithelial cells growing in clusters with tight cell junctions that are surrounded by mouse fibroblast feeder cells (peripheral arrows).

As shown in FIG. 3A, early passage HPECs were able to grow into monolayers, and these cells continued to grow.

Example 2

Harvesting and Culturing of Primary Human Mammary Epithelial Cells (HMECs)

Normal human mammary tissues were collected with the informed consent of the patients or parents. A primary mammary cell suspension was prepared according to well-established procedures in the art. Briefly, mammary tissue was harvested and subjected digestion with a mixture of dispase and collagenase 1A, and subsequently digested with trypsin. Such method of routine isolation and culturing of mammary epithelial cells are found in *Culture of Epithelial Cells* (Ian Freshney and Mary G. Freshney, Eds. Wiley-Liss, Inc.) ($2^{nd}$ Ed. 2002), which is incorporated by reference.

After spinning, the pellet was removed and disbursed and plated in "F medium." F medium is prepared by mixing F-12 (Gibco) in a 3:1 (v/v) ratio with 5% fetal bovine serum, 0.4 μg/ml hydrocortisone, 5 μg/ml insulin, 8.4 ng/ml cholera toxin, 10 ng/ml epithelial growth factor (EGF), 24 μg/ml adenine, 100 U/ml penicillin and 100 μg/ml streptomycin. A ROCK inhibitor, Y027632 was added to the F medium at a concentration of about 10 μM. The cells were plated in the presence of non-proliferating J2 cells that had been gamma irradiated.

The cells were cultured in standard cell culture vessels under normal cells culture conditions, 37° C. at 5% $CO_2$ and normal atmospheric pressure. Medium was changed every 2-3 days.

After the cells reached confluence, the cells were harvested and passaged using standard cell culturing techniques as described in Chapman, S. et al., *J. Clin. Invest.*, 120(7):2619-2626 (2010), which is incorporated by reference.

Figure 3B:
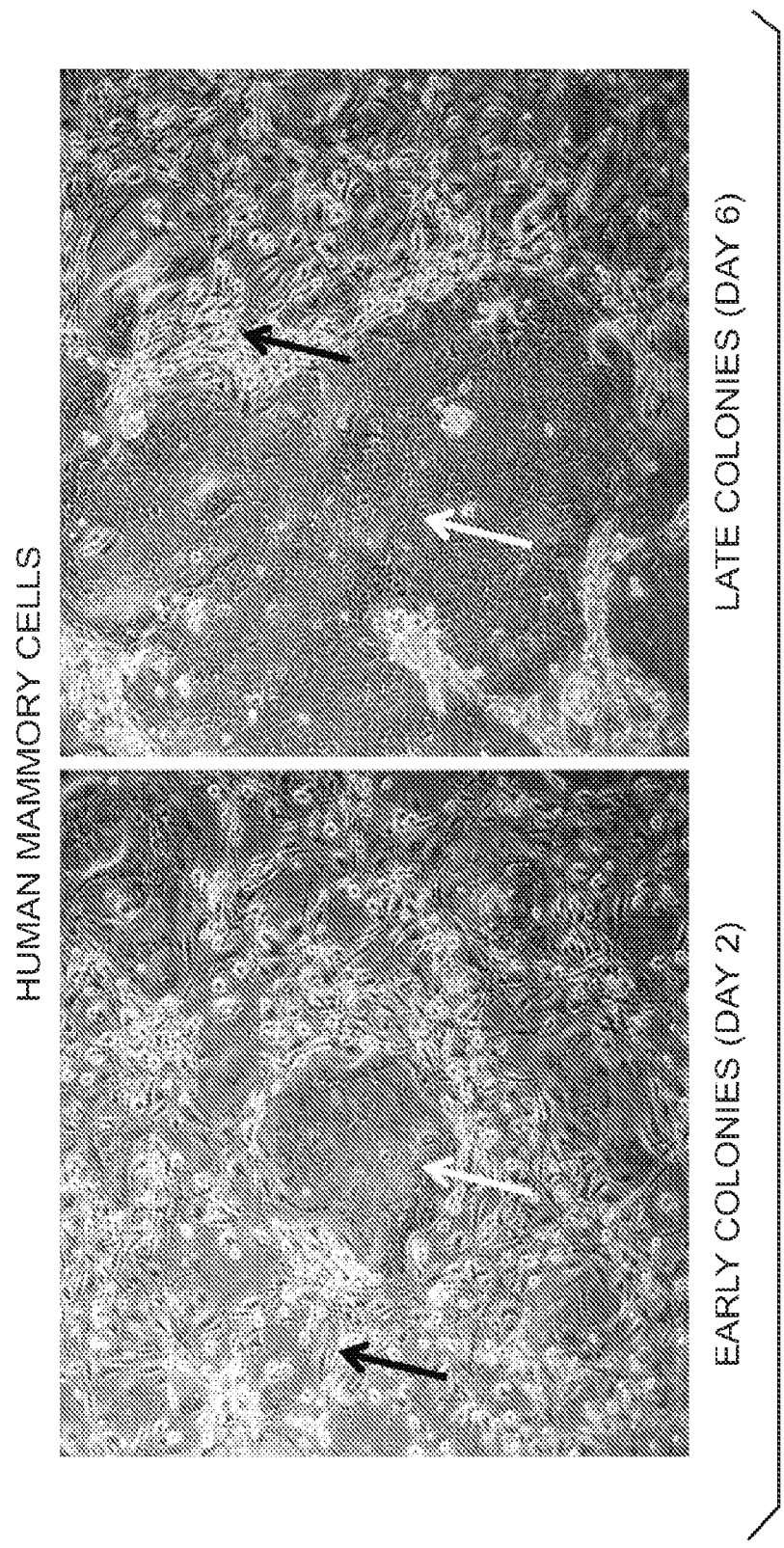
Figure 5B:
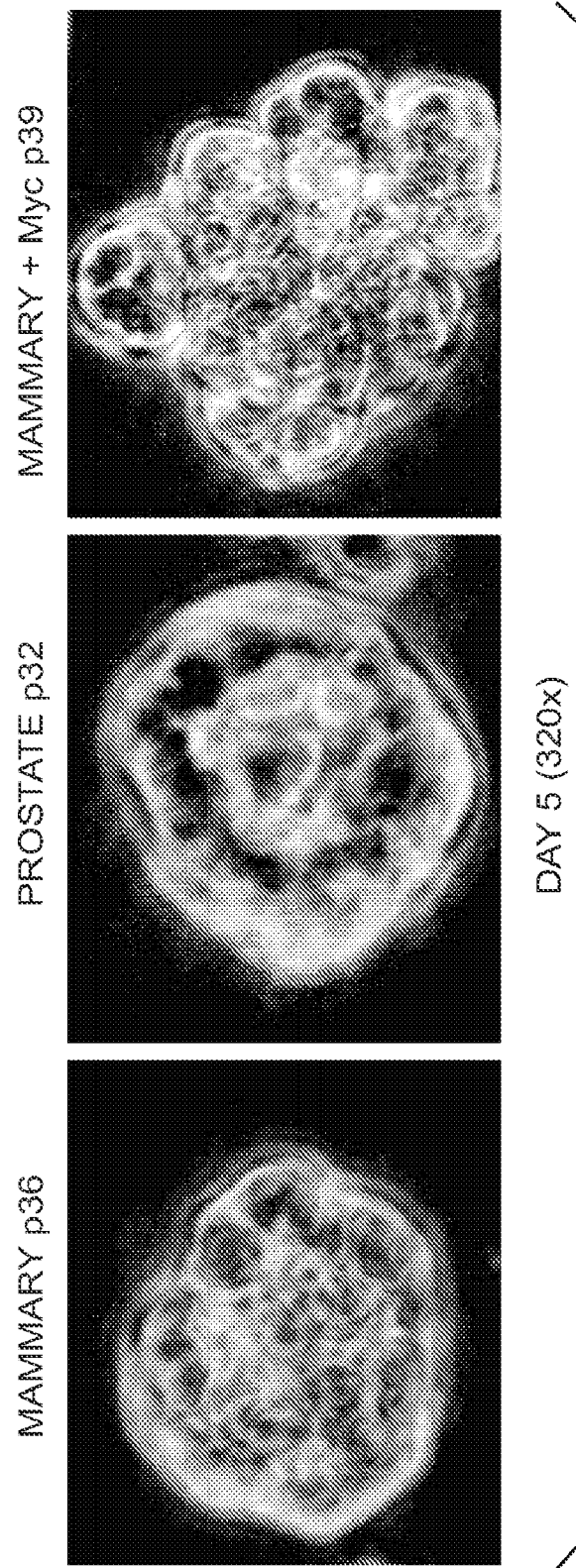
FIG. 5 depicts the morphological architecture of late passage human mammary epithelial cells (HMEC) and human prostate epithelial cells (HPEC) after culturing using the methods and culture conditions disclosed herein. An established immortalized human mammary cell line transformed with a myc mutant was used as a control. The HMECs and HPECs were at passaged for 35 and 31 passages respectively and then plated on a Matrigel®-based three-dimensional cell culture. (A) By day 5, the HMECs and HPECs had begun forming tight colonies organized as multiacinar, spherical structures, whereas the immortalized myc mutant mammary cells formed random, disorganized clumps. Both the HPECs and HMECs formed polarized monolayers at the periphery of each sphere. (B) A magnified view of a representative tight colony of cells on day 5 of culturing on the three-dimensional surface. The multilayer organization of the HMECs and HPECs is clearly seen, and the disorganization the myc mutant cells is also seen. (C) Con-focal microscopy of beta-catenin staining of a cluster of organized HMECs after 5 days of culturing, passage 36, on the three-dimensional cell culture surface.
Figure 5C:
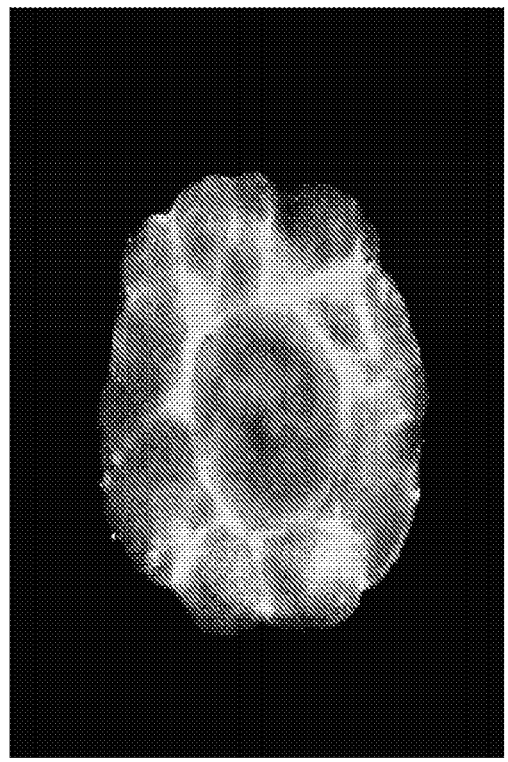

As shown in FIG. 3B, early passage HMECs were able to grow into monolayers, and these cells continued to grow.

Example 3

Comparison of Growth Curves of HMECs and HPECs Under Various Conditions

Figure 2A:
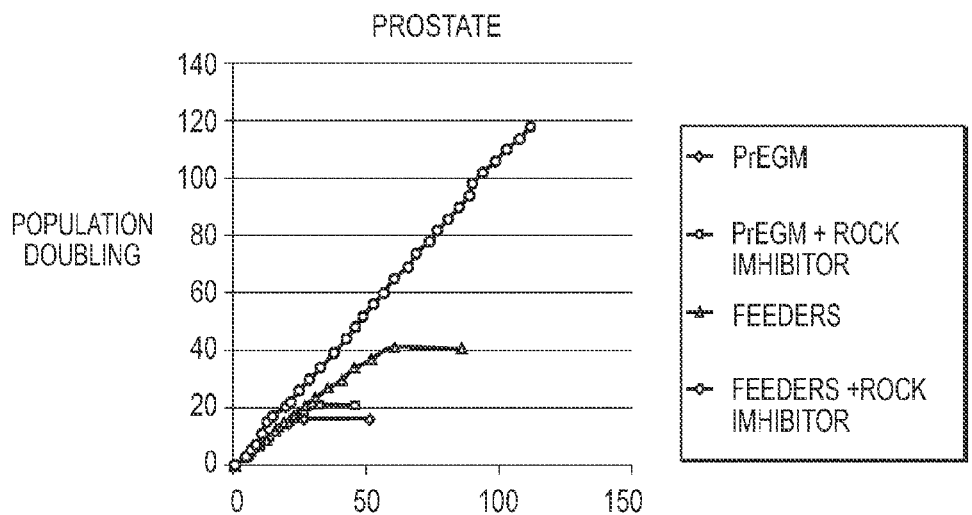
FIG. 2 depicts in vitro growth curves of human primary prostate cells and human primary mammary cells under various growth conditions. PrEGM is a synthetic commercial prostate epithelial cell growth medium; MEGM is a synthetic commercial mammary epithelial cell medium; Feeders are J2 mouse fibroblasts that have been irradiated or treated with mitomycin C; ROCK inhibitor is Y27632 at a concentration of 10 μM that was applied to the cells at initial plating and thereafter. The y-axis is population doublings and the x-axis is number of days. Media was changed every 3 days for all groups.
Figure 2B:
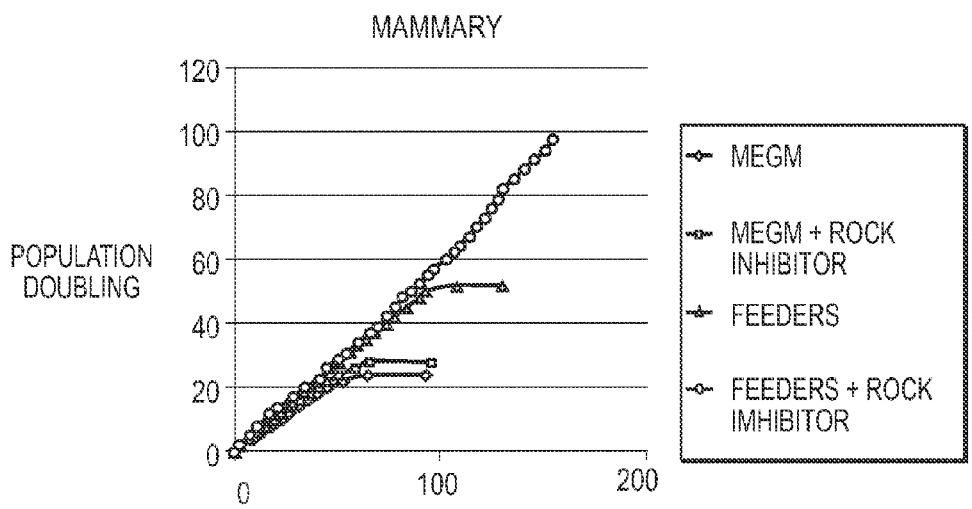

Primary HMECs and HPECs were grown under the four different conditions noted in FIG. 2. Referring to FIG. 2, PrEGM (Lifeline Cell Technology) is a synthetic medium ("Postalife Epithelial Cell Culture Medium") specifically designed for culturing prostate epithelial cells that does not contain serum and where the supplements are synthetic and well defined. MEGM (Lifeline Cell Technology) is a synthetic medium ("Brochialife Epithelial Cell Culture Medium") specifically designed for culturing mammary epithelial cells that does not contain serum and where the supplements are synthetic and well defined. Feeders were the J2 mouse fibroblasts that have been gamma irradiated. The ROCK inhibitor was Y27632 at a concentration of 10 µM that was applied to the cells at initial plating and thereafter. The y-axis is population doublings and the x-axis is number of days. Media was changed every 2-3 days for all groups.

FIG. 2 shows that the primary prostate cells grown in PrEGM stopped growing after about 25 days, and the primary mammary cells grown in MEGM stopped growing after about 50-60 days. The addition of the ROCK inhibitor to the synthetic media did not affect growth. Cells grown in the presence of the feeder cells in F medium without ROCK inhibitor had about the same growth rate, i.e., the slope of the lines was about the same, but the cells grown in the presence of feeder cells eventually stopped growing. Primary cells grown in the presence of feeder cells in F medium and with ROCK inhibitor supplemented have continued to grow.

Example 4

Cell Surface Marker Staining of Late Passage HMECs and HPECs

HPECs, passage 29, and HMECs, passage 32 were grown on sterile glass cover slips and fixed in 4% (wt/vol) paraformaldehyde and labeled with the primary (mouse anti-p63, Santa Cruz, sc-863) and secondary antibody (Alexa Fluor 488 donkey anti-mouse IgG) according to the manufacturer's protocol. DNA in the cells was stained for 3 minutes at room temperature with 0.5 µg/ml Hoescht (no. 33342) in PBS and washed three times with PBS. Coverslips were mounted on glass slides using ProLong anti-fade mounting medium (Invitrogen) for 1 hour at room temperature and were stored at 4° C. A Zeiss Axioskop microscope (Carl Zeiss, Inc., Thornwood, N.Y.) equipped with a 63× objective lens and a Hammamutsu charge-coupled-device camera was used to image the cells. Images were processed using Openlab 3.0.7 software. FIG. 4 demonstrates that the late passage HMECs and HPECs both expressed the basal cell marker p63, while the negative control cells (LnCAPs) did not.

Example 5

Morphological Architecture of Conditionally Immortalized HMECs and HPECs

Conditionally immortalized HPECs (passage 32), HMECs (passage 36) and genetically immortalized HMECs (MycT58A) (passage 39) were transferred to a Matrigel®-based three-dimensional culture.

By day 5 of the 3D culture, the normal, conditionally immortalized HMECs and HPECs formed organized, multiacinar, spherical structures, whereas the genetically immortalized myc mutant mammary cells formed random, disorganized clumps.

A representative cluster of HMECs after 5 days in 3D culture was stained for beta-catenin using standard techniques. Beta catenin is a protein involved in forming adherens junctions, which are necessary to maintain normal layers of epithelial cells. The HMECs stained positively for beta-catenin and displayed organized, multiacinar, spherical structures.

Example 6

Culturing and Expansion Normal and Prostate Tumor Cells from the Same Patient

Figure 6A:
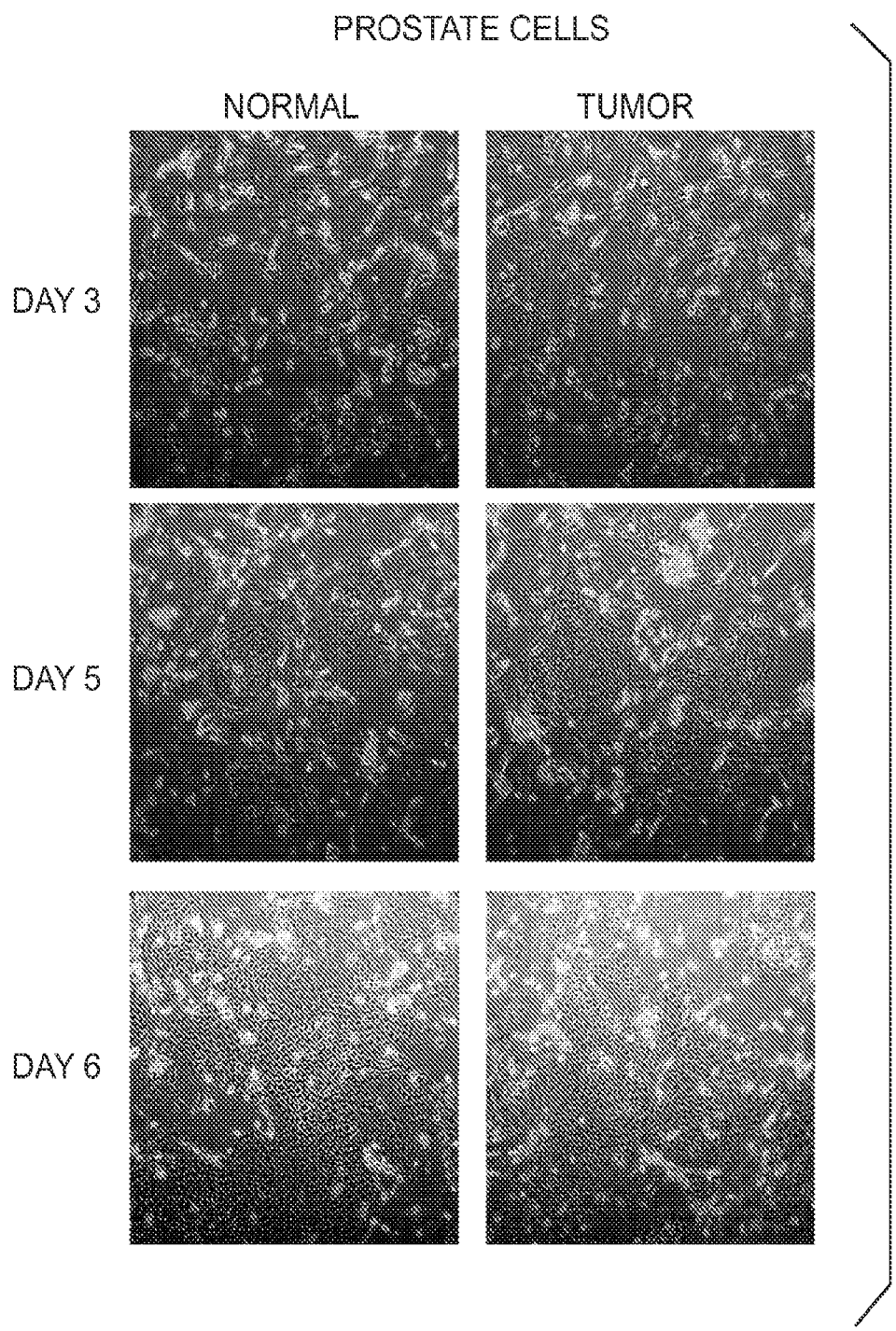
FIG. 6 depicts the growth of normal and tumorigenic human prostate cells using the methods and culture conditions disclosed herein. Both normal and tumor cells had been frozen and this figure is the initial plating after thawing. (A) By day 6, both normal and tumor cells grow well using the methods and culture conditions disclosed herein. (B) The cells from (A) were passaged twice after thawing and then plated on a then plated on a Matrigel®-based three-dimensional cell culture. By day 8, the normal cells had begun forming tight colonies organized, spherical structures as in FIG. 5A and the tumor cells had begun forming random, disorganized clumps of cells.
Figure 6B:
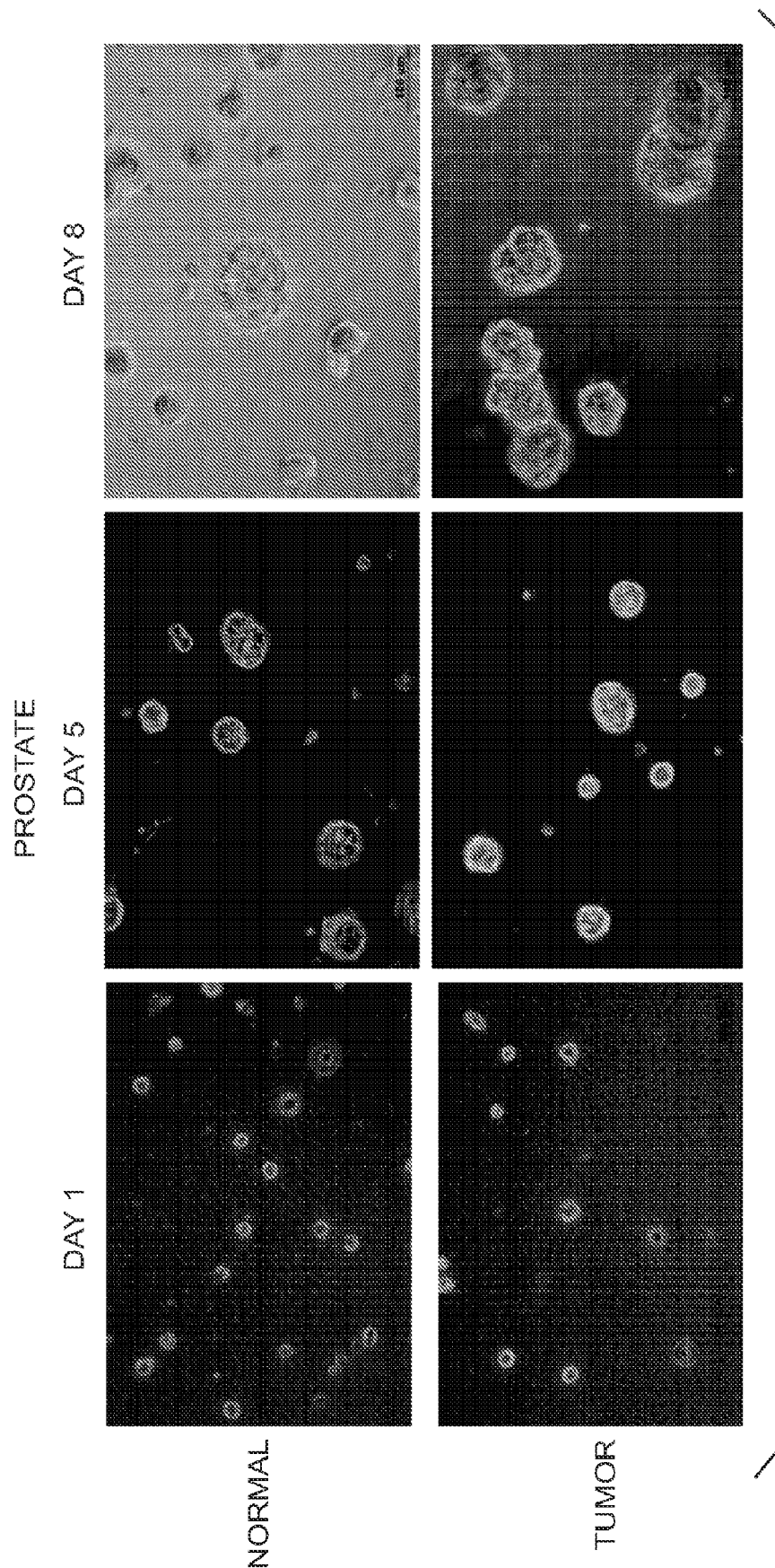
Figure 7B:
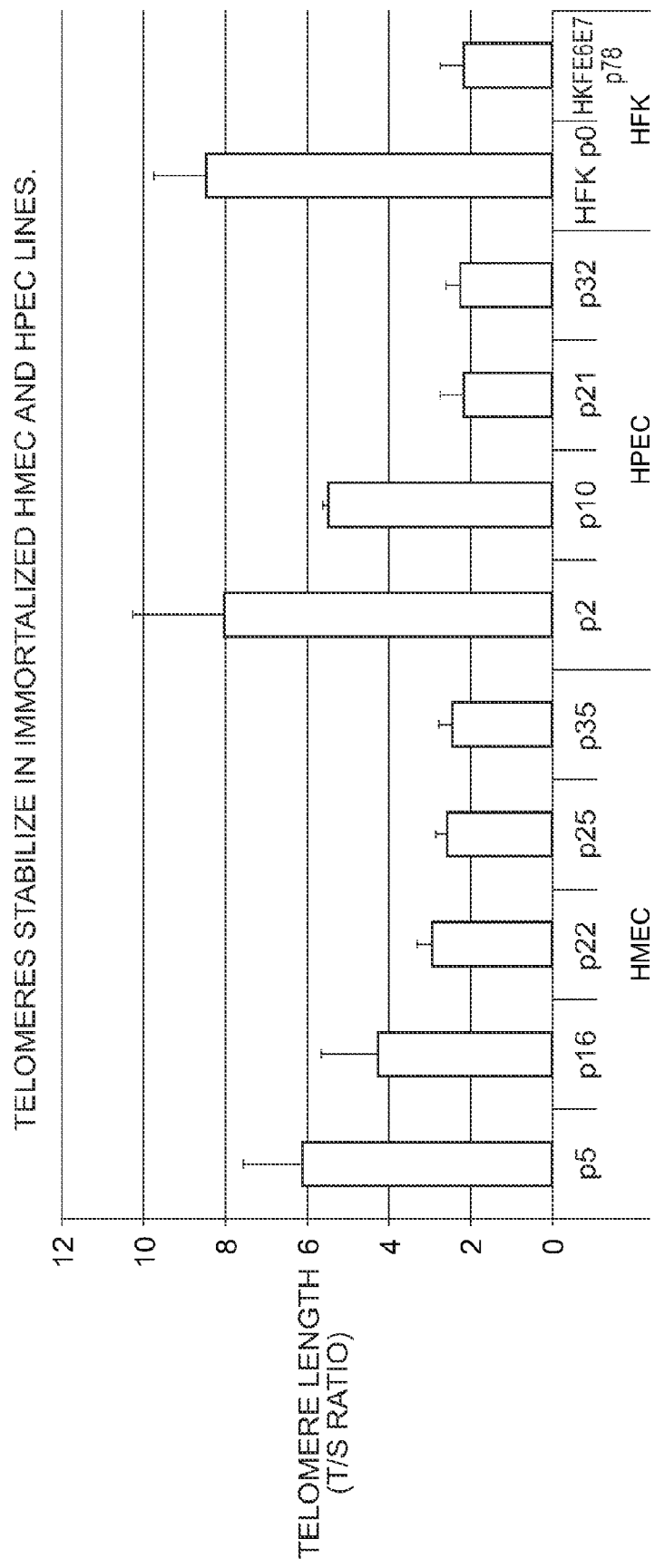
FIG. 7 depicts (A) average levels of telomerase (hTERT) expression and (B) average telomere length at each passage indicated for human mammary epithelial cells (HMECs) and human prostate epithelial cells (HPECs) using the methods and culture conditions disclosed herein. Human foreskin keratinocytes (HFK) transformed with E6E7 from human papilloma virus (HPV) were used as controls and were cultured without a ROCK inhibitor and in serum-free medium. Telomerase activity tends to increase with time and passage number in the HPECs and HMECs, mirroring the telomerase activity of the immortalized, transformed HFK cells. Although telomere length seems to increase over time, the average telomere length decreases over time and stabilizes to an average length of about 2 kB in HMECs and HPECs.
Figure 10:
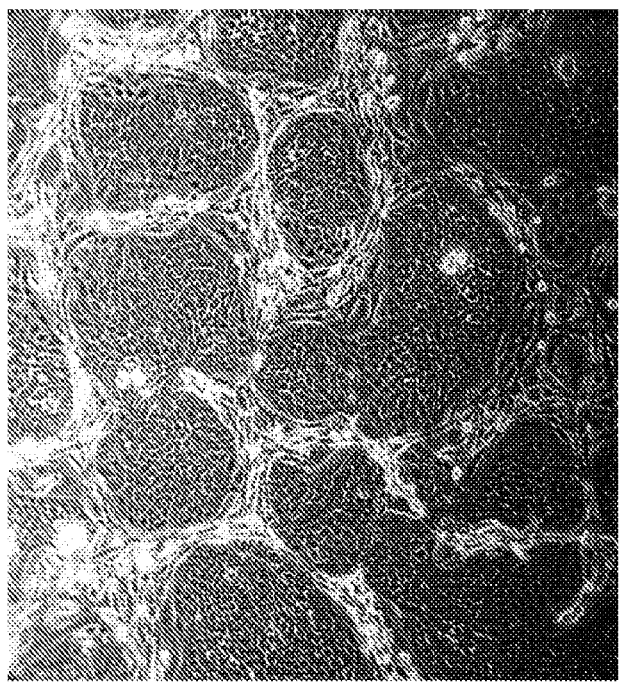
FIG. 10 depicts the growth and maintenance of human tracheal-bronchial epithelial cells using the methods and culture conditions disclosed herein at passage 2. Cells were grown in F medium supplemented with 5% fetal bovine serum and in the presence of the ROCK inhibitor Y27632 at a concentration of 10 μM. At the center of each panel, epithelial cells are growing in clusters that are surrounded by mouse fibroblast feeder cells.

Normal prostate and tumor prostate cells previously harvested and frozen were separately thawed and plated using the conditions described in Example 1 above. As shown in FIG. 6, both sets of cells grow, expand and create a monolayer on the cell culture surface by day six after thawing.

After two passages, the normal and tumor cells were plated on a three-dimensional cell culture as in Example 5 above. Similar, if not identical to the late passage HPECs in Example 5, the thawed normal HPECs formed organized, multiacinar, spherical structures, and the tumor cells formed random, disorganized clumps.

Example 7

Telomerase Activity and Telomere Length of Conditionally Immortalized Cells

Total cellular RNA was isolated with TRIzol reagent (Invitrogen) and treated with a DNA-free kit (Ambion) according to the manufacturer's instructions. First-strand cDNA was synthesized with some modifications using 2 µg of total cellular RNA following the instructions of Superscript First-Strand Synthesis System for RT-PCR (Invitrogen). Taqman real-time QRT-PCR was performed on the Bio-Rad iCycler MyiQ for quantitation of hTERT mRNA using primers and probes sense primer 5'-TGACACCTCACCTCACCCAC-3', antisense primer 5'-CACTGTCTTCCGCAAGTTCAC-3' and Taqman probe 5'-ACCCTGGTCCGAGGTGTCCCT-GAG-3' as previously reported in Fu et al., *Cancer Research* 63, 7815-7824, (2003), which is incorporated by reference. Genomic DNA was extracted from cells using Qiagen DNeasy Blood & Tissue Kit (Cat #69506). Average telomere length was assessed by a modified method of the real-time PCR-based telomere assay described previously in Cawthon R., *Nucleic Acids Res.* 37(3):e21 (2009) and Cawthon R., *Nucleic Acids Res.*, 30(10):e47 (2002), which are incorporated by reference.

Briefly, the telomere repeat copy number to single gene copy number (T/S) ratio was determined using a Bio-Rad IQ5 thermocycler in a 96-well format. Five nanograms of genomic DNA was subjected to PCR reactions with Rio-Rad SYBR Green Super mixture. The primers for telomere length and HBG1 (a single copy gene) were: Tel-15' CGGTTTGTTTGGGTTTGGGTTTGGGTTTGGGTTTG-GGTT-3, and Tel-25'-GGCTTGCCTTACCCTTACCCT-TACCCTTACCCTTACCCT-3'; HBG1 5'-TGTGCTGGC-CCATCACTTTG, and HBG2 5'-ACCAGCCAC-CACTTTCTGATAGG-3'. The reactions proceeded for 1 cycle at 95° C. for 5 min, followed by 41 cycles at 95° C. for 15 s, 60° C. for 45 s. All samples for both the telomere and globin reactions were done in triplicate. In addition to the samples, each 96-well plate contained a six-point standard curve from 0, 0.2, 1, 5, 25, 125 ng using genomic DNA (telomere length 10.4 kb) from Roche Telo-kit. The T/S ratio (dCt) for each sample was calculated by normalizing the average HBG Ct value from the average telomere Ct value.

Example 8

Culturing of Other Types of Non-Keratinocyte Epithelial Cells

Liver tissue (FIG. 8) or mammary tissue (FIG. 9) was collected from mice with different genetic backgrounds. The primary cell suspension was prepared according to the methods of Example 1 and modified as necessary to account for the different cell types according to well-established procedures in the art. Briefly, tissue was harvested and subjected to digestion with a mixture of dispase and collagenase 1A, and subsequently digested with trypsin.

After spinning, the pellet was removed and disbursed and plated in "F medium." F medium is prepared by mixing F-12 and DMEM in a 3:1 (v/v) ratio with 5% fetal bovine serum, 0.4 µg/ml hydrocortisone, 5 µg/ml insulin, 8.4 ng/ml cholera toxin, 10 ng/ml epithelial growth factor (EGF), 24 µg/ml adenine, 100 U/ml penicillin and 100 µg/ml streptomycin. A ROCK inhibitor, Y027632 was added to the F medium at a concentration of about 10 µM. The cells were plated in the presence of J2 feeder cells.

The cells were cultured in standard cell culture vessels under normal cells culture conditions, 37° C. at 5% $CO_2$ and normal atmospheric pressure. Medium was changed every 2-3 days.

After the cells reached confluence, the cells were harvested and passaged using standard cell culturing techniques.

Example 9

Culturing of Human Epithelial Cells from Bronchi

Frozen cells were purchased from Lifeline Cell Technologies and thawed in F medium as used herein above. A ROCK inhibitor, Y027632 was added to the F medium at a concentration of about 10 µM. The cells were plated in the presence of non-proliferating J2 cells that had been gamma irradiated.

The cells were cultured in standard cell culture vessels under normal cells culture conditions, 37° C. at 5% $CO_2$ and normal atmospheric pressure. Medium was changed every 2-3 days.

Example 10

Comparison of Growth Rates Between Conditionally Immortalized HPECs and Normal HPECs HPECs are harvested and cultured according to the methods of Example 1. In parallel, another set of HPECs is harvested and cultured without feeder cells and using a synthetic cell culture medium designed for prostate epithelial cells. Cells cultured under this second set of conditions are referred to as "normal HPECs." Briefly, normal HPECs are grown without feeder cells present in well-defined PrEGM serum-free medium or in keratinocyte serum-free (KSF) medium supplemented with 25 µg/ml of bovine pituitary extract and 0.2 ng/ml of recombinant epidermal growth factor.

After digestion of the tissue, cells from each group are counted and plated at about $1 \times 10^5$ in a 75 cm$^2$ culture flask. The cells are cultured in standard cell culture vessels under normal cells culture conditions, 37° C. at 5% $CO_2$ and normal atmospheric pressure. Medium for each group is changed every 2-3 days depending on growth rates.

After several days, cells are harvested and counted using standard cell culturing techniques. More conditionally immortalized cells are generated than normal cells in either PrEGM or KSF medium, indicating that the culture conditions stimulate growth of HPECs over presently standard conditions.

Example 11

Comparison of Growth Rates Between Conditionally Immortalized HMECs and Normal HMECs HMECs are harvested and cultured according to the methods of Example 2. In parallel, another set of HMECs is harvested and cultured without feeder cells and using a synthetic cell culture medium designed for prostate epithelial cells. Cells cultured under this second set of conditions are referred to as "normal HMECs." Briefly, normal HMECs are grown without feeder cells present in well-defined MEGM serum-free medium or in keratinocyte serum-free (KSF) medium supplemented with 25 µg/ml of bovine pituitary extract and 0.2 ng/ml of recombinant epidermal growth factor.

After digestion of the tissue, cells from each group are counted and plated at about $1 \times 10^5$ in a 75 cm$^2$ culture flask. Cells were plated with a total of about 10,000 cells per well. The cells are cultured in standard cell culture vessels under normal cells culture conditions, 37° C. at 5% $CO_2$ and normal atmospheric pressure. Medium for each group is changed every 2-3 days.

After several days, cells are harvested and counted using standard cell culturing techniques. More conditionally immortalized cells are generated than normal cells in either MEGM or KSF medium, indicating that the culture conditions stimulate growth of HMECs over presently standard conditions.

Examples 10 and 11 can be repeated for any type of NKE, such as but not limited to hepatocytes, pancreatic cells and the like.

Example 12

Identification of Candidate Therapeutic Agents for an Individual

Figure 12:
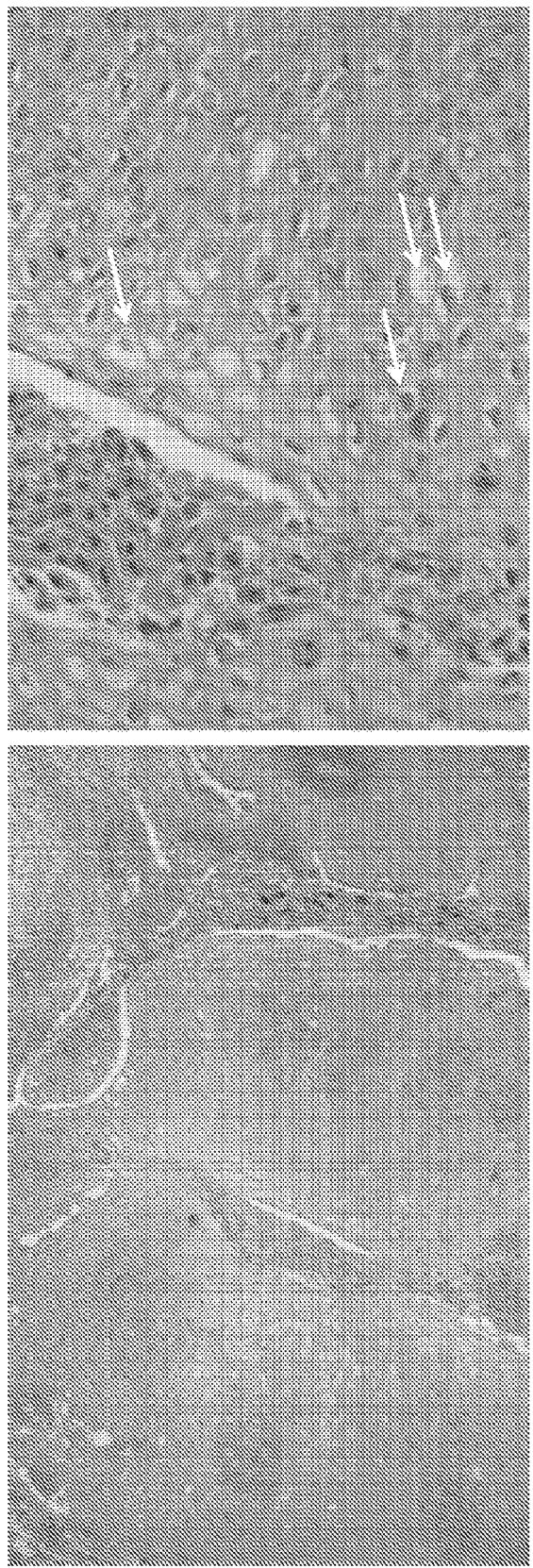
FIG. 12 depicts histological sections of a resected specimen demonstrating the presence of a squamous papilloma with koilocytotic atypia from tissue taken from the upper right lobe of the subject's lungs.

A 22 year old male patient with recurrent papillomatosis of the larynx for 16 years was chosen for this study. The disease progressively involved not only the larynx, but had spread to the upper airway (trachea and bronchi) and recently into the lung parenchyma. The patient had had more than 350 surgeries. Besides surgeries, multiple treatments had failed, including interferon treatment (1996-2010), Methotrexate (2001-03), intralesional Cidofovir (2007-2010), and intralesional Avastin (2010). A CT scan revealed that there were multiple pulmonary nodules in 2008. By October 2010, the size each lung lesion examined was increasing. During the last surgical intervention, a wedge resection of the right upper lobe was performed to remove metastatic tumor. Pathologic analysis of the resected specimen demonstrated the presence of a squamous papilloma with koilocytotic atypia (FIG. 12). Koilocytotic changes in such tumors are an indication that the tumor is producing infectious HPV. However, at the time of intervention, the type of HPV involved in this tumor had not been identified. Since the tumor had not responded to several different treatment modalities, it was also unclear how the patient would be treated following surgery.

Figure 13:
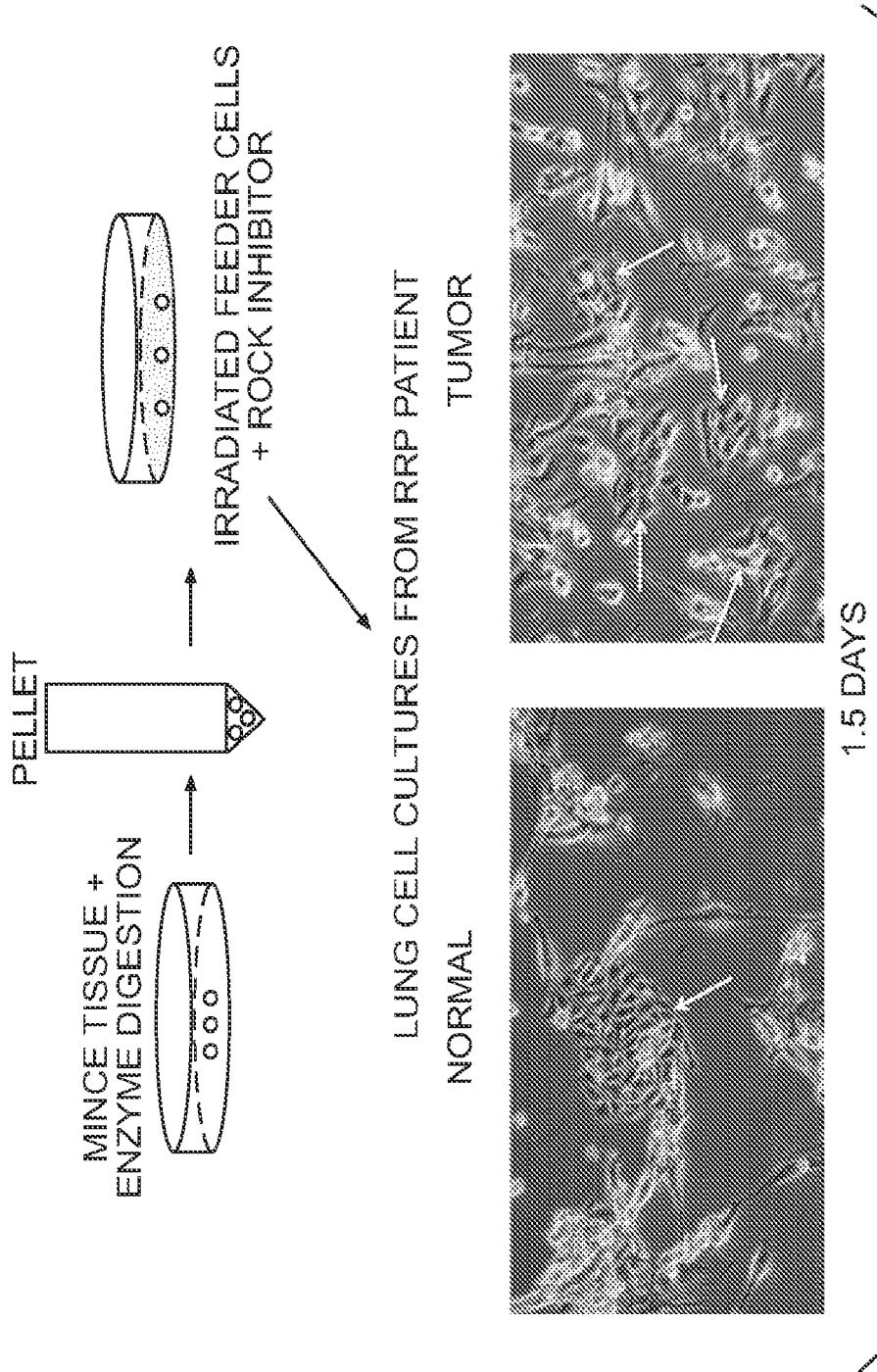
FIG. 13 depicts the processing of the tissue biopsy taken for both normal and tumor tissue for generating cell lines.
Figure 14:
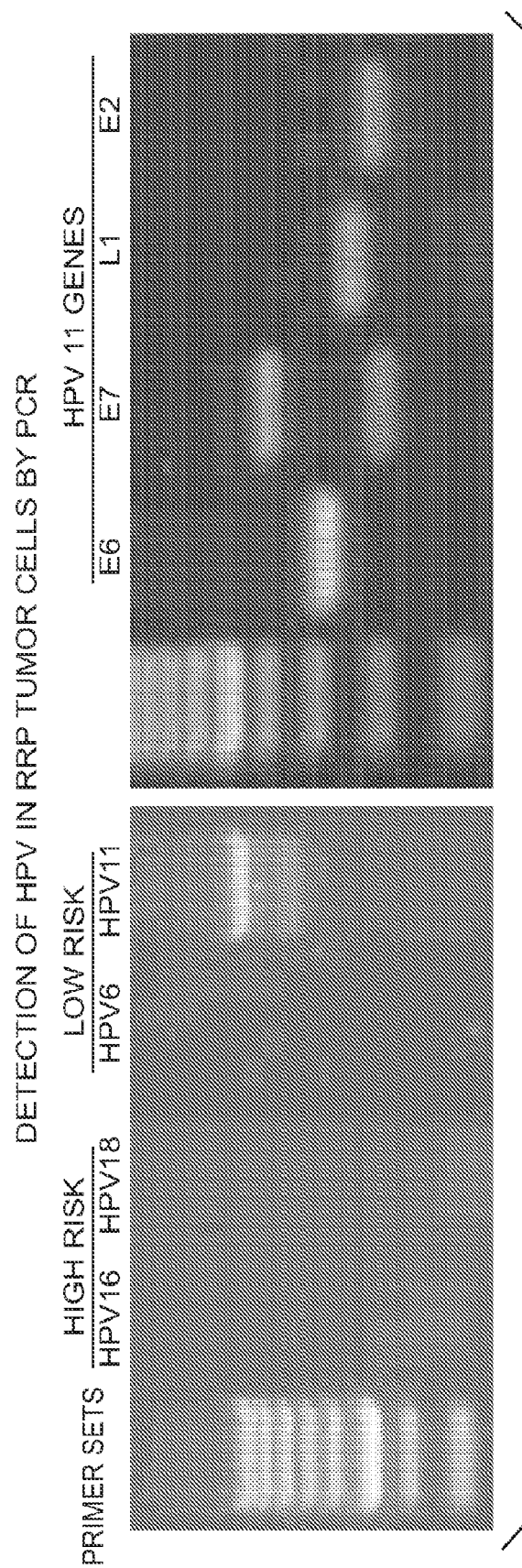
FIG. 14 depicts analysis of DNA that was extracted from the cultured tumor cells. Primers specific for various types of human papillomavirus (HPV) and PCR were used to evaluate whether low risk HPVs (HPV-6, HPV-11) or high risk HPVs (HPV-16 or HPV-18) were present. Only the low-risk HPV-11 DNA was detected.

A small biopsy was obtained of the lung tumor (and normal lung tissue) at the time of surgery and the tissue was processed to generate cell lines (FIG. 13). Using the cell culture methods described herein, cell lines were generated from both normal and tumor tissue, which were then used to determine what type of HPV was the etiologic agent in this tumor. As shown in FIG. 14, DNA was extracted from the tumor cells and specific primers and PCR were to evaluate whether low risk HPVs (HPV-6, HPV-11) or high risk HPVs (HPV-16 or HPV-18) were present. Only the low-risk HPV-11 DNA was detected.

Figure 15:
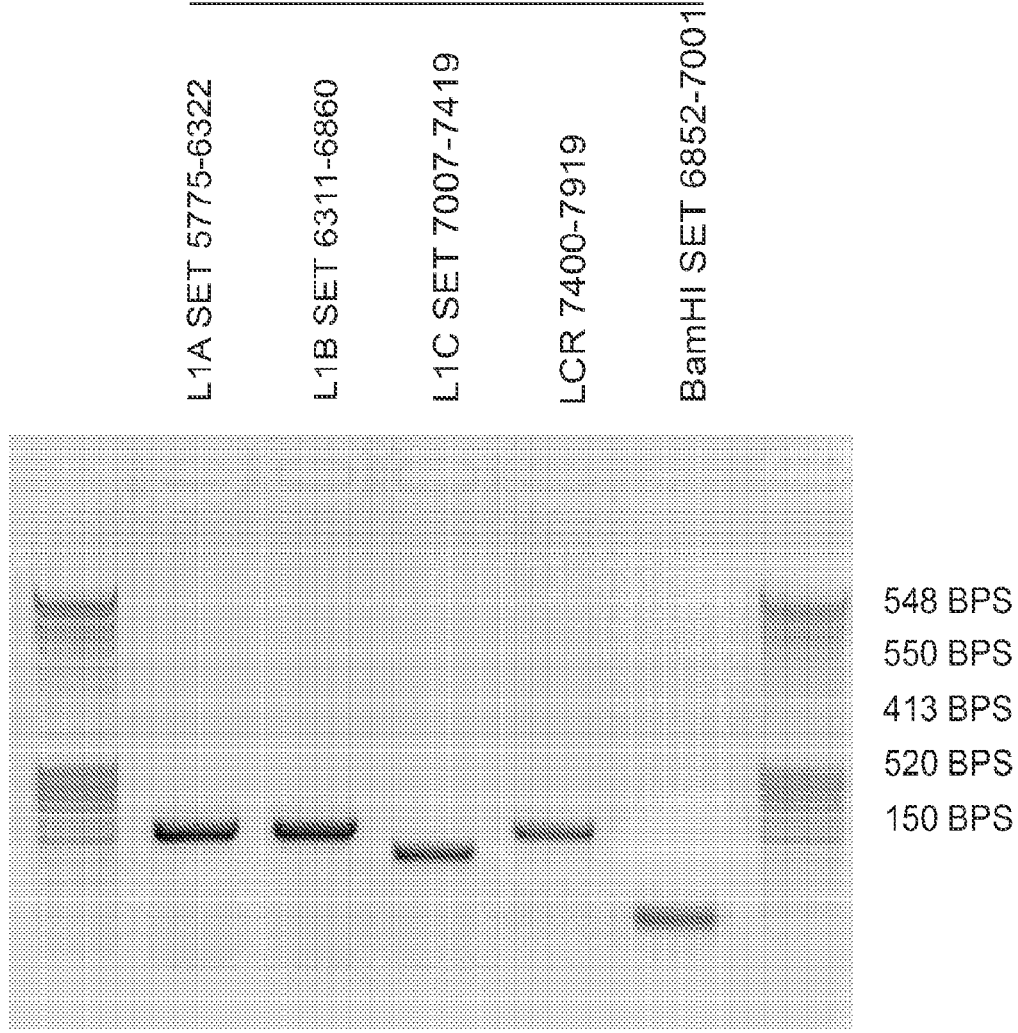
FIG. 15 depicts analysis of DNA that was extracted from the cultured tumor cells to determine if the HPV-11 virus was carrying the L1 gene. The presence or absence of the L1 gene would indicate that an anti-L1 vaccine might be useful in the management of this patient. The data indicate that the entire L1 gene (from by 5775-7001) was found intact in the abnormal NKE cells.
Figure 16:
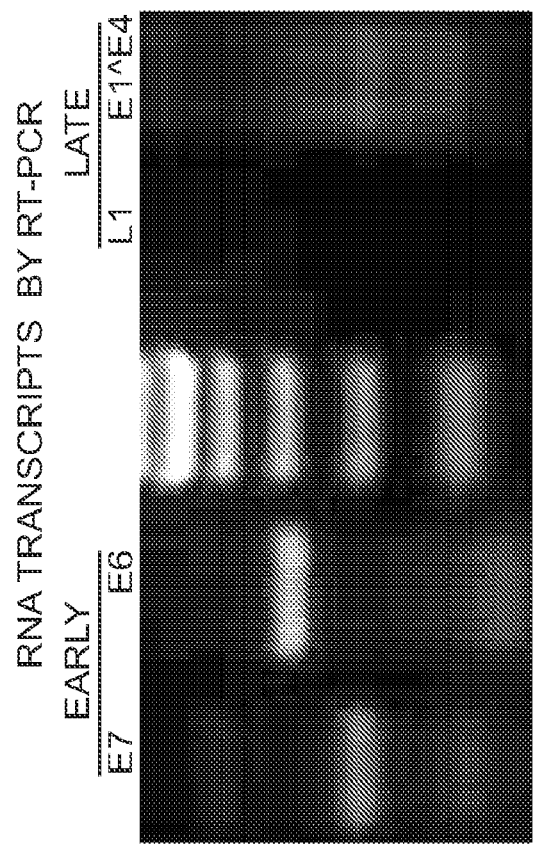
FIG. 16 depicts an analysis of mRNA being produced in the abnormal NKE cells taken from the subject during biopsy and being cultured according to the methods of the present invention. It was verified that these early and late genes were being transcribed into mRNA.

A portion of the HPV-11 DNA was sequenced to determine if both the early and late regions of the genome were intact. It was clear that both the E6 and E7 early transforming genes were present as well as the L1 late gene (a viral capsid protein). "Primer walking" was also utilized to evaluate whether the entire L1 gene was present. The presence or absence of the L1 gene was useful to determine if an anti-L1 vaccine might be used in the management of this patient. The data in FIG. 15 indicate that the entire L1 gene (from by 5775-7001) was found intact in the abnormal NKE cells. Finally, it was verified that these early and late genes were being transcribed into mRNA. FIG. 16 shows that the early E6 and E7 transforming genes were being transcribed but that the L1 gene was not. This was a critical finding, since the use of the HPV vaccine (based on L1 protein) would not be helpful for this patient since the L1 protein was not being produced. Accordingly, based on this genetic analysis, it was determined that alternative ways to treat the tumor should be used.

Total DNA was isolated from the patient's cultured cells or tissue using DNeasy Blood & Tissue Kit (Qiagen). The DNA was amplified using an Illustra TempliPhi RCA kit (GE Healthcare). The products were digested with BamHI, and cloned into pUC19 vector. Viral genomes were sequenced from two directions using Primer Walking Services (Genewiz).

Real-time quantitative PCR was performed using a Taq-Mann™ kit on a Bio-Rad iCycler MyiQ, using primers and probes for the quantification of HPV11 L2 (sense primer, 5'-TGACACCTCACCTCACCCAC-3'; anti-sense primer, 5-CACTGTCTTCCGCAAGTTCAC-3'; and TaqMan probe, 5'-ACCCTGGTCCGAGGTGTCCCTGAG-3'). Human R-Globin Gene was used as an endogenous reference in each reaction. Real-time PCR reactions were done in triplicate for all samples. The levels of HPV DNA were analyzed using iQ5 software with the normalized expression ({Delta}{Delta}CT) method according to the manufacturer's (Bio-Rad's) guidelines.

Most RRP cases are caused by HPV6 or HPV11. Several studies have shown that HPV11 is usually considered as the more aggressive one, and the majority of RRP with lung involvement were caused by HPV11. General HPV detection primers and HPV type-specific primers were used to HPV typing assay. To confirm the HPV11 infection, Rolling Circle Amplification (RCA) was used to amplify the episomal HPV DNA. Surprisingly, the restriction digestion did not match the typical HPV11 pattern. Instead of one BamHI site for the prototype HPV11, the viral genome isolated from pulmonary tumor cells had two BamHI sites. More important, the size of the viral genome was estimated more than 10 kb. Most HPVs have genome size around 8 kb, and the size of prototype HPV11 is 7931 base pairs. Additional restriction enzyme digestion revealed that, besides BamHI, the enzymes AatII, AgeI, FspI, XcmI and pPuMI in the region of L1-LCR-E6-E7-E1 all cut viral genome twice instead of just once. All the other single-digestion enzyme sites of HPV11 were retained as a single site on the viral genome, suggesting that the viral DNA may have a duplication of L1-LCR-E6-E7-E1. To determine the details of the duplication, the whole viral genome cloned into vector pUC19 and the viral genome was sequenced from two directions. Sequencing data were verified and submitted to GenBank (accession number JN644141). The HPV11 in the pulmonary tumor cells had an episomal genome the length of 10,424 base pairs. The confirmed duplication sequence in the length of 2493 base pairs included partial L1-LCR-E6-E7-partial E1 sequences. The duplicated sequences were annotated as L1(B), LCR(B), E6(B), E7(B) and E1(B). To address whether the patient was infected with the mutated virus or the mutation happened in the patient during disease progression, viral genome from patient's laryngeal tissue was isolated. The viral genome from larynx was also cloned and sequenced (GenBank accession number JN644142). The viral genome at the original infection site was very similar to the prototype HPV11 in the size of 7933 base pairs, and with no duplication, suggesting that the viral genome mutations accompanied tumor progression of recurrent respiratory papillomatosis. Viral titers were measured using quantitative real time PCR, and the pulmonary tumor cells contained 7-fold more HPV genomes than the laryngeal lesions. Viral genome was calculated at about 40.16 copies of viral DNA per cell in lung, and about 5.74 copies of viral DNA per cell in the larynx.

Figure 17A:
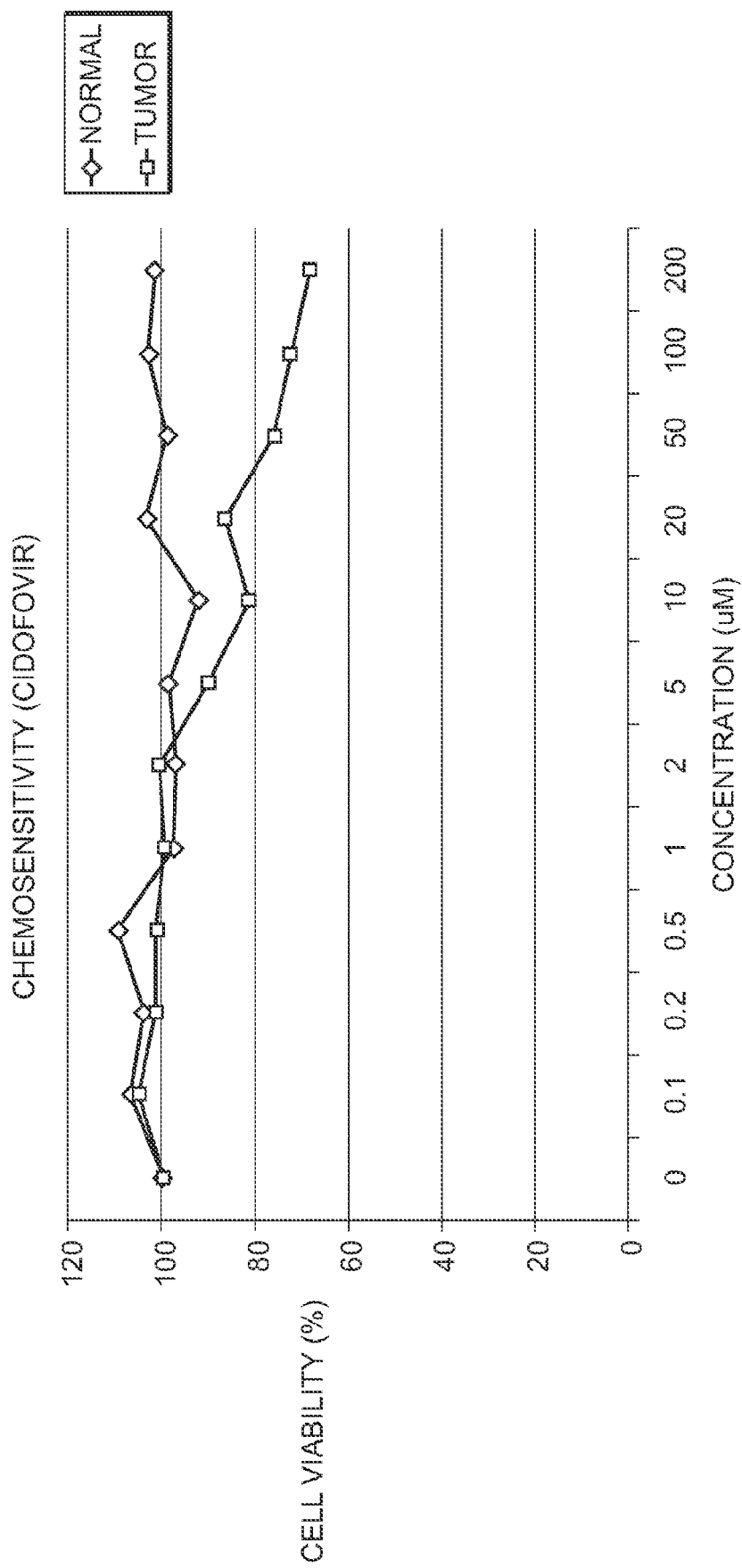
FIG. 17 depicts cell viability curves that were generated using abnormal NKE cells taken from the subject during biopsy and being cultured according to the methods of the present invention in response to Cidofovir (A) an HDAC inhibitor (SAHA, Vorinostat) (B), and an artemisinin derivative (DHA) (C). Normal and tumor cells were treated with Cidofovir, Vorinostat or DHA at indicated concentration for 24 hours. Cell viabilities were measured using CellTiter-Glo® Luminescent Cell Viability Assay (Promega)
Figure 17B:
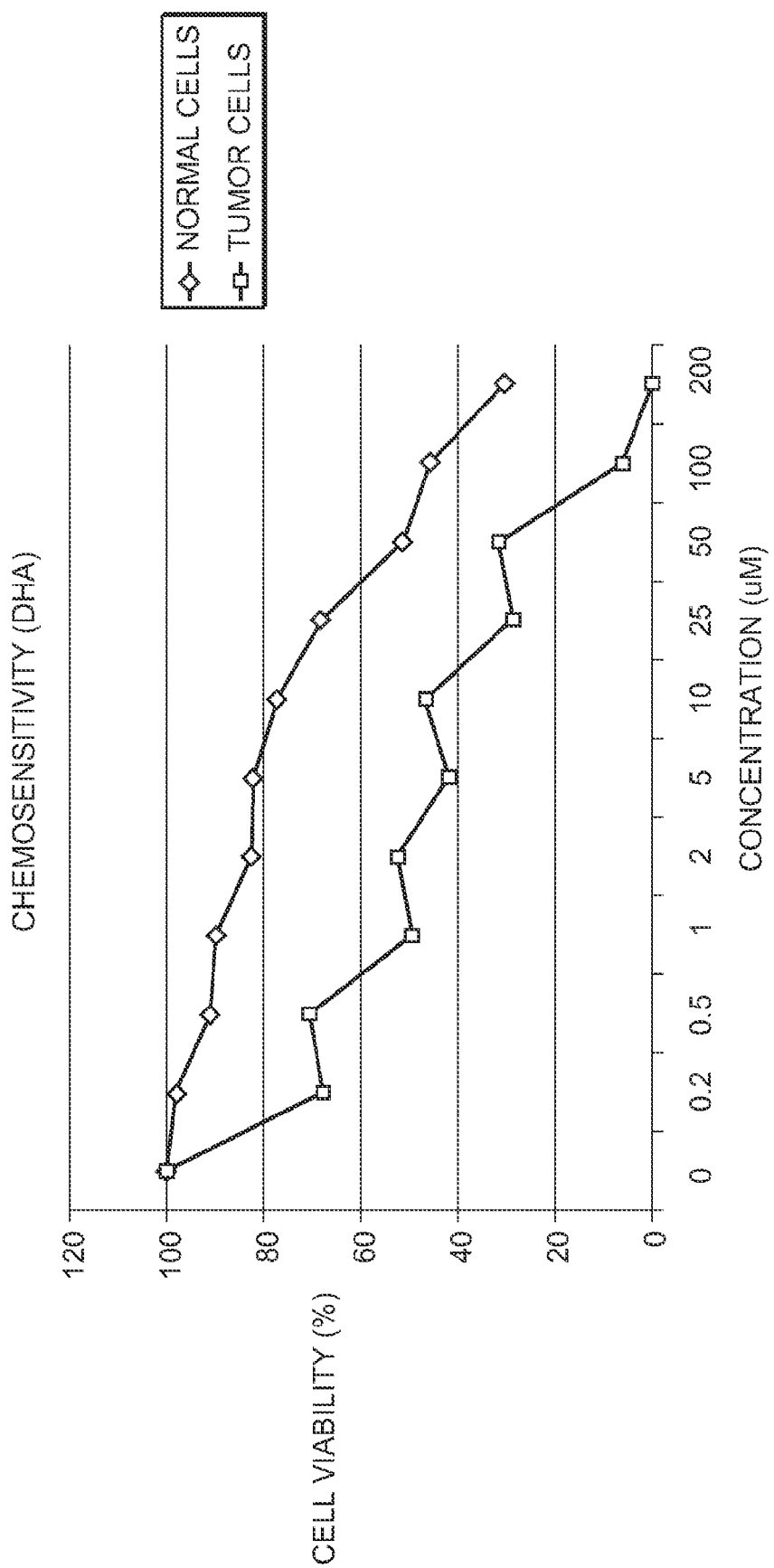
Figure 17C:
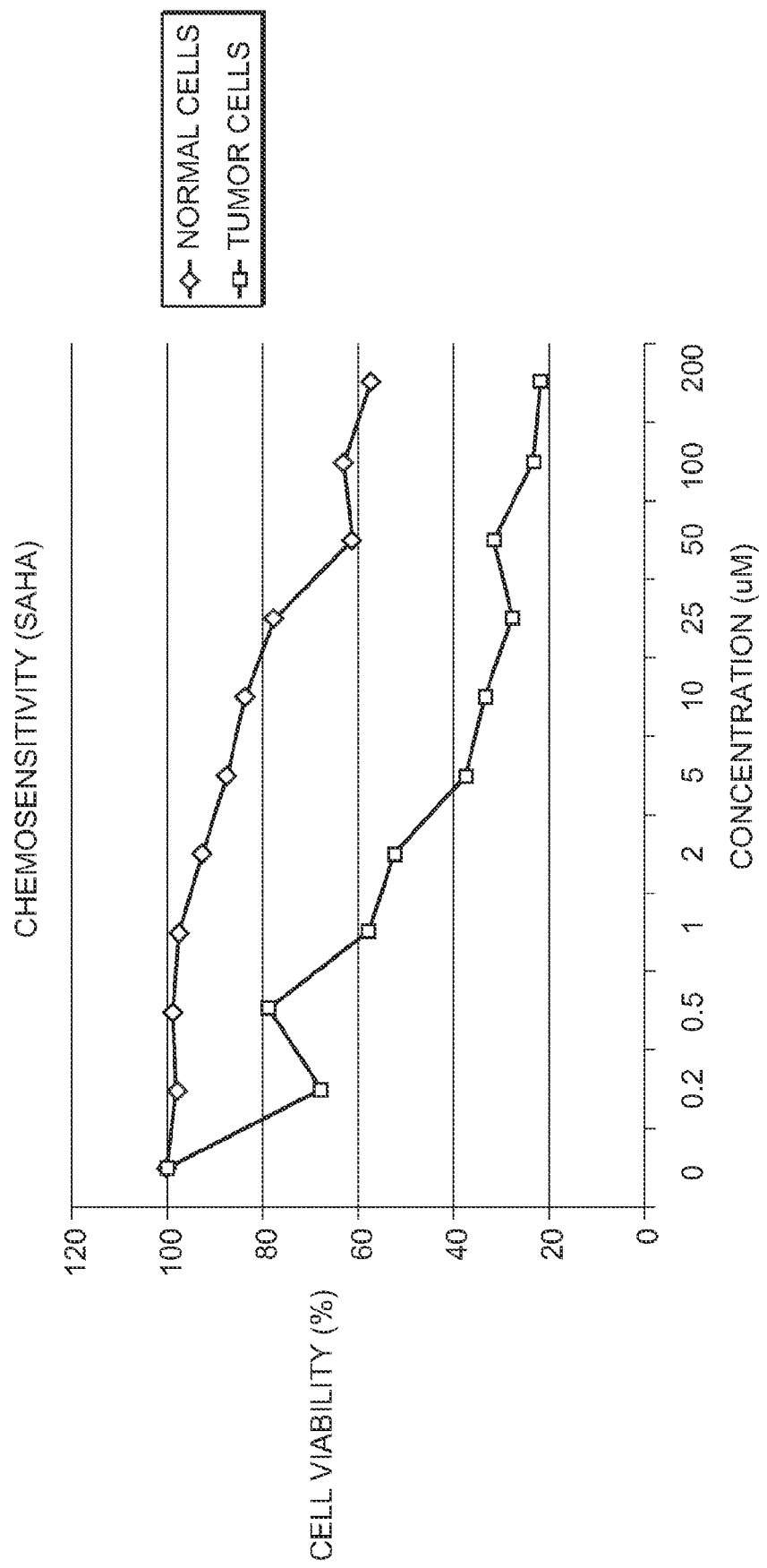

Previous studies have shown that artemisinin derivatives (DHA and artesunate) and the HDAC inhibitor (SAHA) are able to efficiently kill cervical cancer cells that express the high-risk HPVs. There is no data in the literature, however, analyzing the effect of these inhibitors on cells containing low-risk HPVs, because there are no cell lines established that contain HPV-6 or HPV-11. The cell culture methods have allowed the establishment of a cell line expressing HPV-11. More importantly, this cell line was used to evaluate the sensitivity to the above inhibitors and to compare it to the sensitivity of normal lung cells isolated from the same patient (FIG. 17).

It is clear that the HPV-11-containing tumor cells from the patient are approximately 100-fold more sensitive to DHA and SAHA than the normal lung cells. For example, the $EC_{50}$ for SAHA is 2 μM and the $LD_{50}$ is approximately 200 μM. The therapeutic index is defined as $LD_{50}/EC_{50}$ and, in this case, it equals 100. This value represents an excellent therapeutic index and suggests that SAHA may represent a viable pharmaceutical for treatment. The same was true for DHA, although the therapeutic index for DHA was not 100. Cidovovir is the most common drug used for treating RRP. Interestingly, Cidofovir (FIG. 17A) was completely ineffective in vitro even at very high concentrations (50-200 μM).

Based on the in vitro sensitivity data, the patient was placed on Vorinostat therapy in January of 2011. The therapy consisted 4 week cycle (3 weeks on, 1 week off) of Vorinostat at 400 mg/daily. A subsequent CT scan in revealed very encouraging results in that no new lesions were identified, smaller lesions were shrinking, and some larger lesions were also decreasing in size. A more recent CT scan showed that all lesions had stabilized, and no major side effects had been observed. Thus, the use of the cell culture methods of the present invention were critical in determining a response profile of the abnormal cells, which enabled the identification of at least two chemotherapeutic agents that might be useful for treating this patient's tumors. Using the cell culture methods of the present invention, the response profile, including the genetic analysis and the therapeutic index, was generated within one week of biopsy.

Example 13

Establishment of a Cell Line from a Single Needle Biopsy

Figure 18:
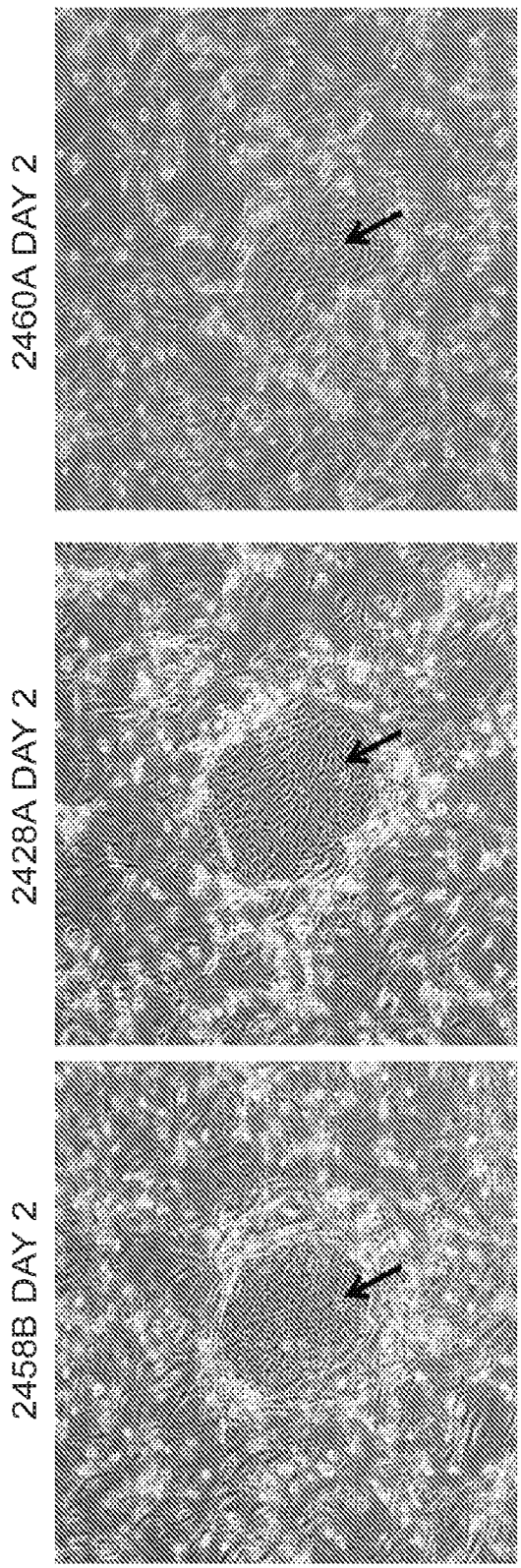
FIG. 18 depicts expansion of cells from a needle biopsy specimen from a rat breast tumor using the cell culture methods of the present invention. By day 2, the rat mammary tumor cells were proliferating well and a cell line was established that could be used in vitro studies.

In a separate experiment, a needle biopsy specimen from a rat breast tumor was used in the cell culture methods of the present invention. The rat mammary tumor cells proliferated well and a cell line was established that could be used in vitro studies (FIG. 18). Thus, a sufficient number of tumor cells to generate cell lines was obtained in a single needle biopsy. This will greatly expand the capability for performing genetic, biochemical and molecular studies on very small clinical samples. For example. in the case of breast tumors, evaluation of needle biopsies is currently confined to H&E and IHC staining of the sample because there have not been any methods of expanding and culturing these cells until now.

The Examples of Embodiments disclosed herein are meant to be illustrative and are not intended to limit the scope of the present invention in any manner.

Example 14

Establishment of a Cell Line after Freezing and Thawing

Figure 19:
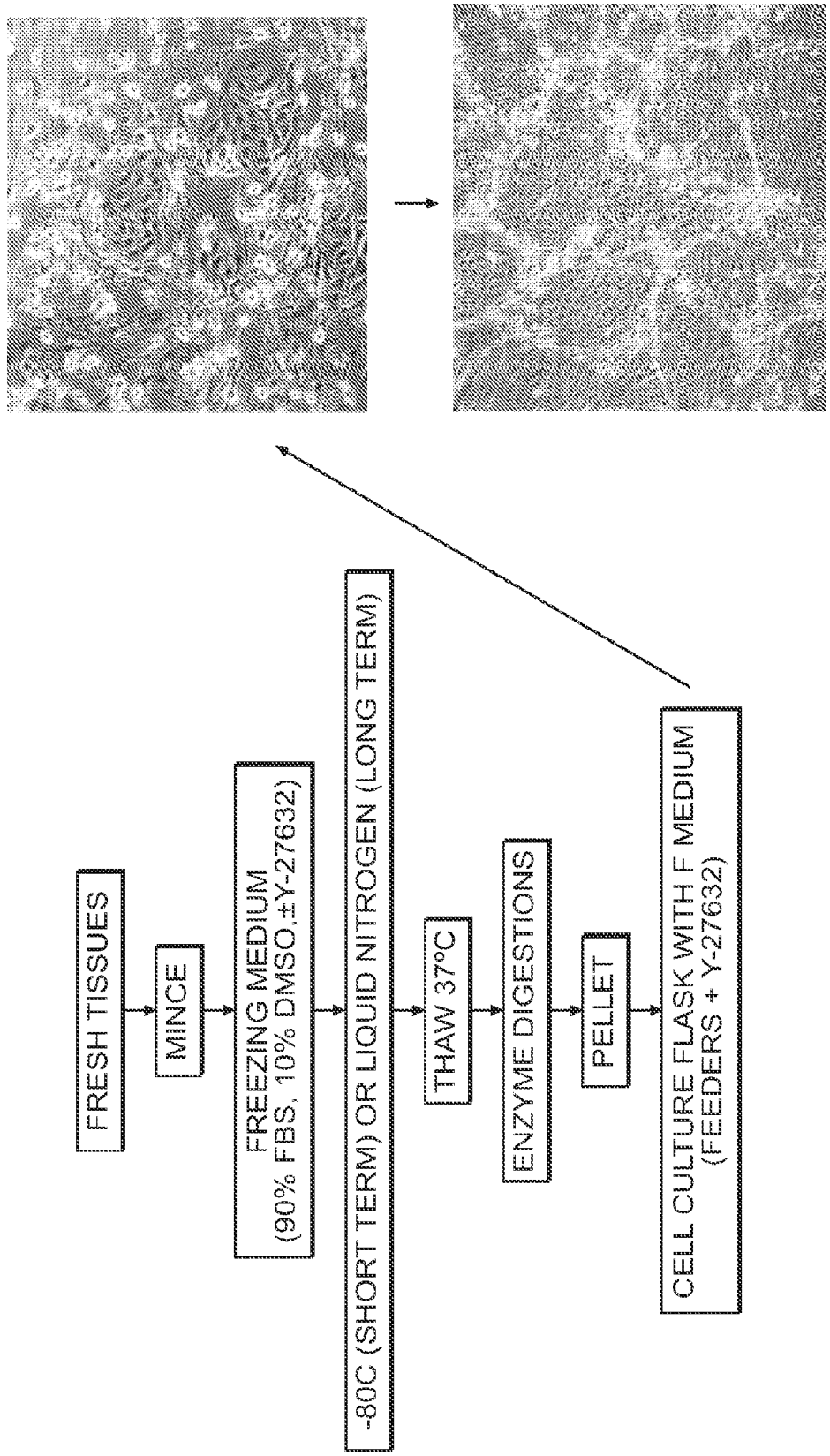
FIG. 19 depicts a flow chart of one of embodiment of the methods of the present invention and photographs of the cells after several days in culture.

Fresh human breast tissue from a reduction mammoplasty patient was minced into small pieces or thin slices with maximal size of 1-3 mm. The tissue pieces were then frozen in 90% fetal calf serum/10% DMSO (v/v)/5 µM Y-27632 at −80° C. or in liquid nitrogen. The frozen tissue was thawed at 37 C, pelleted and suspended in F medium for brief digestion with dispase/collagenase. The cell suspensions were subjected to the culture system as described above. Cell culture photographs (FIG. 19) were taken 5 days (upper panel) and 8 days (lower panel) after plating.

Example 15

Establishment of a Cell Line from Circulating Tumor Cells (CTCs)

Figure 22:
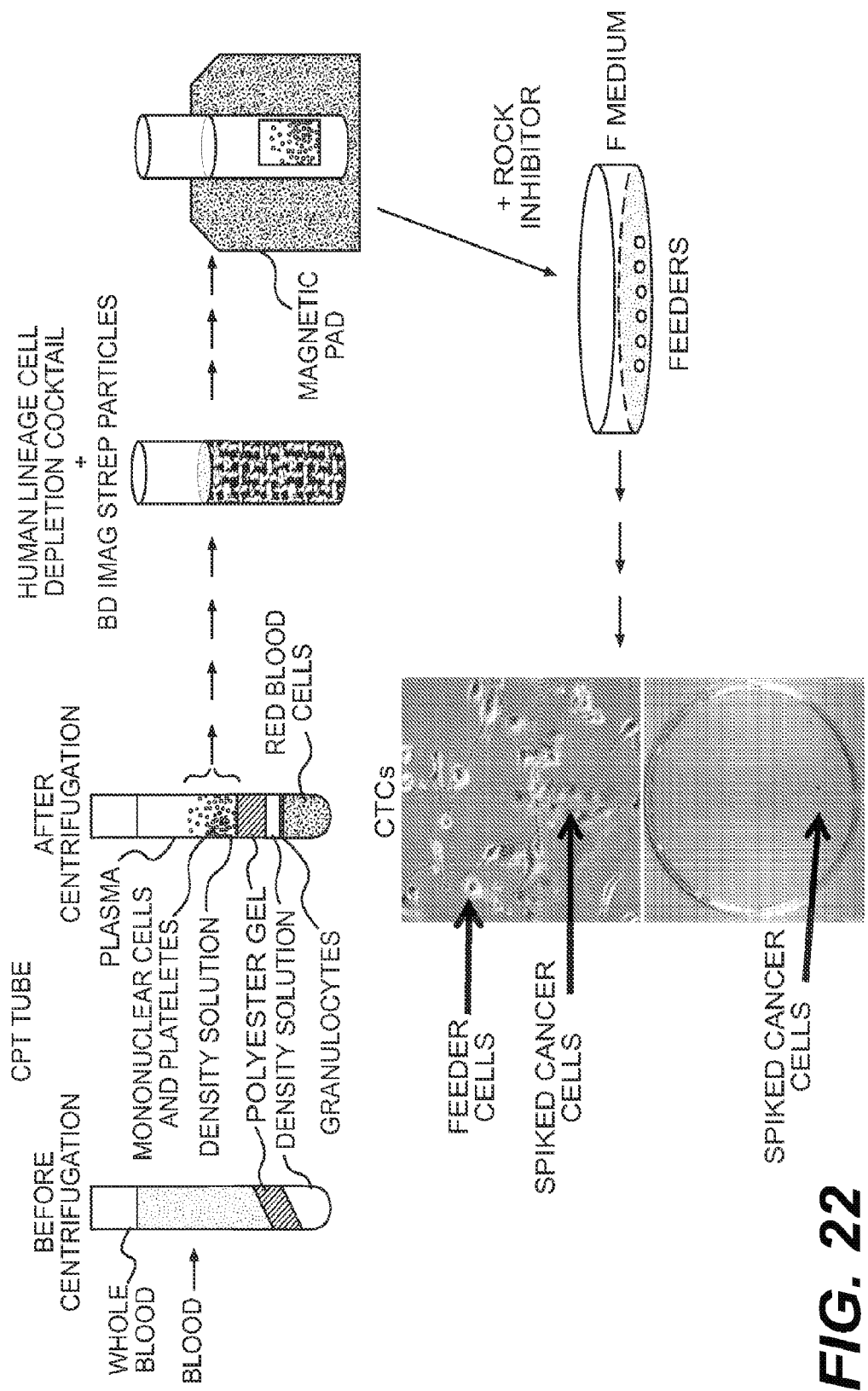
FIG. 22 depicts a protocol for isolating and culturing circulating tumor cells (CTCs).

7 ml of human blood sample was drawn from a health donor and injected to CPT tube (BD Vacutainer® CPT™ Cell Preparation Tubes with Sodium HeparinN). LnCAP (a prostate cancer cell line) cells (between 50-1000 total cells) were spiked into blood sample after collection. The sample was centrifuged at room temperature in a horizontal rotor centrifuge for a minimum of 15 minutes at 1500 to 1800 RCF (Relative Centrifugal Force). After centrifugation, mononuclear cells and platelets were located in the whitish layer just under the plasma layer (see CPT tube). Approximately half of the plasma was aspirated, taking care not to disturb the cell layer. The cell layer was then collected with a Pasteur Pipette and transferred to a 15 mL size conical centrifuge "U" bottom tube with a cap. Human Lineage Cell Depletion Cocktail (Cat #: 51-9005225) was added to the tube, mixed and allowed to sit at room temperature for about 15 minutes. After sitting, about 12 ml 1×PBS was added to the tube and the tube was spun at about 1000 rmp. The supernatant was aspirated. IMag Streptavidin Particles Plus-DM (Becton, Dickinson: Cat #: 51-9003746) were vortexed and the cell pellet was mixed thoroughly with 75 µl of IMag particles. The mixture was allowed to incubate at room temperature for about 30 minutes. After incubation, 1 ml 1×PBS was added to the tube and mixed, and the tube was placed on the BD IMagnet for 6 min. The supernatant was transferred to a new tube. The remaining portion of the tube attached to the BD IMagnet was again mixed with 1 ml PBS. This second supernatant was transferred to another new tube. The two tubes were spun down the pellets were resuspended 3 ml of F medium (+Y-27632) and placed into a 6 well plate with feeder cells. FIG. 22 shows that the spiked tumor cells were recovered from the blood and that these cells began to form colonies after being subjected to the culture conditions described herein.

What is claimed is:

1. A method of continuously culturing non-keratinocyte epithelial cells, the method comprising
    a) culturing the non-keratinocyte epithelial cells in the presence of feeder cells and a calcium-containing medium, and
    b) inhibiting the activity of Rho kinase (ROCK) in the feeder cell, the non-keratinocyte epithelial cells or both during culturing,
    wherein the continuously cultured non-keratinocyte epithelial cells are not embryonic or adult stem cells and the continuously cultured non-keratinocyte epithelial cells become conditionally immortalized.

2. The method of claim 1, wherein the non-keratinocyte epithelial cells are selected from the group consisting of squamous cells, columnar cells, adenomatous cells and transitional epithelial cells.

3. The method of claim 2, wherein the non-keratinocyte epithelial cells are selected from the group consisting of prostate cells, mammary cells, hepatocytes, pancreatic islet cells, pulmonary epithelial cells, kidney cells, bladder cells, stomach epithelial cells, large intestinal epithelial cells, small intestinal epithelial cells, urethral epithelial cells, testicular epithelial cells, ovarian epithelial cells, thyroid cells, parathyroid cells, adrenal cells, *thymus* cells, gall bladder cells and pituitary cells.

4. The method of claim 1, wherein the calcium-containing medium comprises serum or a serum replacement.

5. The method of claim 1, wherein the feeder cells are proliferating or non-proliferating fibroblasts.

6. The method of claim 1, wherein inhibiting the activity of ROCK comprises culturing the non-keratinocyte epithelial cells in the presence of a small molecule inhibitor of Rho kinase 1 (ROCK 1), Rho kinase 2 (ROCK 2) or both.

7. The method of claim 6, wherein the small molecule ROCK 1 or ROCK 2 inhibitor is selected from the group consisting of Y-27632, HA1100 hydrochloride, HA1077 and GSK429286.

8. The method of claim 1, wherein inhibiting the activity of ROCK comprises genetic manipulation of the expression of Rho kinase 1 (ROCK 1), Rho kinase 2 (ROCK 2) or both.

9. The method of claim 1, further comprising passaging the non-keratinocyte epithelial cells after inhibiting ROCK, and placing the passaged cells in cell culture environment in which ROCK is not being inhibited, wherein the cells are no longer conditionally immortalized after the cells are placed in the environment in which ROCK is not being inhibited.

10. The method of claim 9, wherein the environment in which ROCK is not being inhibited is a three-dimensional cell culture environment.

* * * * *